(12) United States Patent
Lee et al.

(10) Patent No.: US 10,835,499 B2
(45) Date of Patent: Nov. 17, 2020

(54) SYSTEMS AND METHODS FOR LONG TERM TRANSDERMAL ADMINISTRATION

(71) Applicant: Corium, Inc., Menlo Park, CA (US)

(72) Inventors: Eun Soo Lee, Redwood City, CA (US); Amit K. Jain, Milpitas, CA (US); Parminder Singh, Union City, CA (US)

(73) Assignee: Corium, Inc., Menlo Park, CA (US)

( * ) Notice: Subject to any disclaimer, the term of this patent is extended or adjusted under 35 U.S.C. 154(b) by 506 days.

(21) Appl. No.: 15/396,252

(22) Filed: Dec. 30, 2016

(65) Prior Publication Data

US 2017/0189348 A1    Jul. 6, 2017

Related U.S. Application Data

(60) Provisional application No. 62/367,055, filed on Jul. 26, 2016, provisional application No. 62/273,288, filed on Dec. 30, 2015.

(51) Int. Cl.
| | | |
|---|---|---|
| *A61K 9/70* | (2006.01) |
| *A61M 35/00* | (2006.01) |
| *A61K 9/00* | (2006.01) |
| *A61K 41/00* | (2020.01) |
| *A61K 47/34* | (2017.01) |

(52) U.S. Cl.
CPC .......... *A61K 9/7084* (2013.01); *A61K 9/0014* (2013.01); *A61K 9/7053* (2013.01); *A61K 9/7061* (2013.01); *A61K 9/7069* (2013.01); *A61K 41/00* (2013.01); *A61K 47/34* (2013.01); *A61M 35/00* (2013.01); *A61K 9/703* (2013.01)

(58) Field of Classification Search
CPC .. A61K 9/7084; A61K 9/0014; A61K 9/7053; A61K 9/7061; A61K 9/7069; A61K 41/00; A61K 47/34; A61K 9/703; A61M 35/00; A61L 15/58; A61L 15/42; A61L 15/225; A61L 2420/08; A61F 13/0259; A61F 13/0253; A61F 13/0243; A61F 5/443; A61F 13/0246; A61F 2013/53925
See application file for complete search history.

(56) References Cited

U.S. PATENT DOCUMENTS

| | | | |
|---|---|---|---|
| 1,683,347 | A | 1/1929 | Clarke et al. |
| 1,880,560 | A | 9/1929 | Gray et al. |
| 1,880,808 | A | 10/1932 | Webber et al. |
| 1,984,147 | A | 12/1934 | Malm |
| 2,129,052 | A | 9/1938 | Fordyce |
| 3,617,201 | A | 11/1971 | Berni et al. |

(Continued)

FOREIGN PATENT DOCUMENTS

| | | |
|---|---|---|
| CA | 2332012 A1 | 11/1999 |
| IE | 61005 B1 | 9/1994 |

(Continued)

OTHER PUBLICATIONS

International Search Report from International Patent Application No. PCT/US2016/069558 dated Apr. 26, 2017.

*Primary Examiner* — Ophelia A Hawthorne
(74) *Attorney, Agent, or Firm* — McDermott, Will & Emery LLP; Judy M. Mohr

(57) ABSTRACT

Devices, systems, compositions and methods for long term or prolonged transdermal administration of an active agent are provided.

18 Claims, 6 Drawing Sheets

(56) References Cited

U.S. PATENT DOCUMENTS

| | | | |
|---|---|---|---|
| 4,787,888 A * | 11/1988 | Fox | A61K 41/0047 |
| | | | 601/2 |
| 5,071,656 A | 12/1991 | Lee et al. | |
| 5,123,900 A * | 6/1992 | Wick | A61F 13/023 |
| | | | 602/41 |
| 5,132,115 A | 7/1992 | Wolter et al. | |
| 5,246,705 A | 9/1993 | Venkatraman et al. | |
| 5,284,660 A | 2/1994 | Lee et al. | |
| 5,614,211 A * | 3/1997 | Gale | A61K 9/7084 |
| | | | 424/448 |
| 5,660,178 A * | 8/1997 | Kantner | C09J 171/00 |
| | | | 600/391 |
| 5,662,925 A | 9/1997 | Ebert et al. | |
| 5,843,468 A | 12/1998 | Burkoth et al. | |
| 6,174,545 B1 | 1/2001 | Enscore et al. | |
| 7,824,707 B2 | 11/2010 | Hille et al. | |
| 8,481,059 B2 | 7/2013 | Cleary et al. | |
| 8,486,443 B2 | 7/2013 | Schumacher et al. | |
| 8,728,445 B2 | 5/2014 | Cleary et al. | |
| 8,815,281 B2 | 8/2014 | Kanios et al. | |
| 9,078,833 B2 | 7/2015 | Audett | |
| 9,622,986 B2 | 4/2017 | Im et al. | |
| 2004/0024028 A1 | 2/2004 | Burton | |
| 2009/0311199 A1 | 12/2009 | Hillman | |
| 2014/0052081 A1 | 2/2014 | Yang et al. | |
| 2014/0276479 A1 | 9/2014 | Nguyen et al. | |
| 2014/0303574 A1 | 10/2014 | Knutson | |
| 2016/0051486 A1 | 2/2016 | Choi et al. | |

FOREIGN PATENT DOCUMENTS

| | | |
|---|---|---|
| JP | 2008259629 A | 10/2008 |
| WO | WO 2009/026135 A2 | 2/2009 |
| WO | WO 2016/099198 A1 | 6/2016 |

\* cited by examiner

SYSTEMS AND METHODS FOR LONG TERM TRANSDERMAL ADMINISTRATION

CROSS-REFERENCE TO RELATED APPLICATIONS

This application claims the benefit of U.S. Provisional Application No. 62/273,288, filed Dec. 30, 2015, this application also claims the benefit of U.S. Provisional Application No. 62/367,055, filed Jul. 26, 2016, both of which are incorporated herein by reference in their entirety.

TECHNICAL FIELD

The subject matter described herein relates to a transdermal delivery system comprising a backing for improved long term administration. The subject matter described herein further relates to a transdermal delivery system comprising at least one segmented layer for improved long term administration. The delivery system is suitable for prolonged administration of an active or therapeutic agent with improved adhesion to the skin at an administration site.

BACKGROUND

Transdermal delivery systems have become more desirable as they have the advantage of avoiding difficulties associated with gastrointestinal absorption of an active agent (e.g. effect of gastrointestinal pH and/or enzyme activity on the active agent, drug-food interactions, gastrointestinal side effects, eliminates pulsed entry into system circulation, and avoid high first-pass effect through the liver). Transdermal delivery systems may also increase patient compliance due to the ability for the patient to self-administer and avoids more invasive treatments such as injections. Transdermal delivery may advantageously provide controlled, constant delivery of the active agent, which may result in less fluctuation in circulating levels of the agent as compared to oral delivery.

Long term administration of transdermal patches is challenging, especially for patches that use occlusive backings. Most transdermal patches cannot remain adhered to the skin or other administration site for an extended period of time, e.g. at least or about 7 days. However, continuous contact of the patch with the patient's skin is necessary for proper drug delivery from the patch. The FDA lists problems associated with transdermal patches which includes the patch not flexing or conforming to the skin; the patch not sticking or the edges of the patch curling after 24 hours (www.fda.gov). Disadhesion may alter or prevent delivery of the drug from the patch. Friction between the layers of the patch and the administration site may also cause the patch to buckle, wrinkle, and/or fail by losing contact with the skin. To address these problems, transdermal patches that are approved for long term use are of small size (e.g. less than 25 cm$^2$) such as the Catapres® or Ortho Evra® patches or require an over-sized overlay to cover the patch. The use of an overlay increases patch size and results in about a 1.5-2 or 2-3 fold increase in the total patch area. Therefore, use of an overlay is only practical for relatively small patches (e.g. not more than about 40 cm$^2$). Many of the multi-day use patch manufacturers recommend using medical tape to secure the patch. For example, the patient instructions for the fentanyl Duragesic® patch recommends applying first aid tape at the edges or use of adhesive dressings as a patch overlay to prevent the problem of patches that do not stick to the skin properly (see www.duragesic.com).

Another approach to long term transdermal patches is the use of a relatively breathable backing layer to increase wear time. Success with these patches is limited as the increased breathability of the backing layer reduces drug flux requiring an increase in total patch area.

Therefore, there exists a need for transdermal compositions, devices and methods that address at least these shortcomings.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

It is an object of the present invention to provide methods and compositions to effect long term or prolonged transdermal delivery of an active agent.

In embodiments, the transdermal patch comprises a first backing layer; an interfacing adhesive layer; a second backing layer comprised of a plurality of segments that are at least partially separated; an adhesive active agent layer comprising at least one active agent; and a release liner. In embodiments, the first backing layer is comprised of an elastic material. In embodiments, the second backing layer and the adhesive active agent layer together comprise a composite layer where the composite layer is comprised of a plurality of segments that are at least partially separated. In some embodiments, the plurality of segments are at least partially connected. In embodiments, at least the first backing layer and the interfacing adhesive layers are laminated. In some embodiments, the layers of the composite layer are laminated. In embodiments, the adhesive active agent layer is comprised of an adhesive matrix.

In embodiments, the first backing layer is comprised of an elastic polymer film, a multi-directional elastic woven fabric, a multi-directional elastic nonwoven fabric, a stretchable polymer film, a stretchable woven fabric, or a stretchable nonwoven fabric. In embodiments, the polymer fabric or polymer film is comprised of one or more polymers selected from polyesters, polyethylenes, polypropylenes, polyvinylchloride, polyethylene vinyl acetate or copolymers thereof, and polyurethanes. In some embodiments, the first backing layer has a thickness of about 0.2-50 mil.

In embodiments, the interfacing adhesive layer is comprised of one or more polymers selected from selected from acrylates, acrylate copolymers, polyisobutylene, silicone, polystyrene butyl rubber, polyethylene vinyl acetate and copolymers thereof, and plasticized polymers. In embodiments, the interfacing adhesive layer comprises a first adhesive layer adjacent the first backing layer and a second adhesive layer adjacent the second backing layer.

In embodiments, the second backing layer is comprised of a material selected from an occlusive material and a breathable material. In embodiments, the second backing layer is comprised of one or more polymers selected from polyesters, polyethylenes, polypropylenes, polystyrenes, polyvinylchloride, and a polyethylene terephthalate/ethylene vinyl acetate laminate.

In embodiments, the composite layer further comprises a tie layer positioned distal to the adhesive active agent layer. In embodiments, the tie layer is a rate-controlling membrane that controls the rate of active agent release.

In embodiments, the composite layer further comprises a contact adhesive layer positioned between the adhesive active agent layer and the release liner. In some embodiments, each segment of the composite layer has a size of about 2-40 cm².

In embodiments, at least the first backing layer and the release liner are sized to extend about 0.5-1.0 cm beyond the perimeter of the composite adhesive layer.

In embodiments, the release liner is comprised of a material selected from a silicone coated material, a fluorocarbon coated material, and a fluorosilicone coated material.

In a further aspect, a method of transdermally administering an active agent is provided. In embodiments, the method comprises removing a release liner from the transdermal patch as described herein; and adhering the transdermal patch to the skin of a patient for a period up to about 10 days to deliver the active agent to said patient.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

Figure 1:
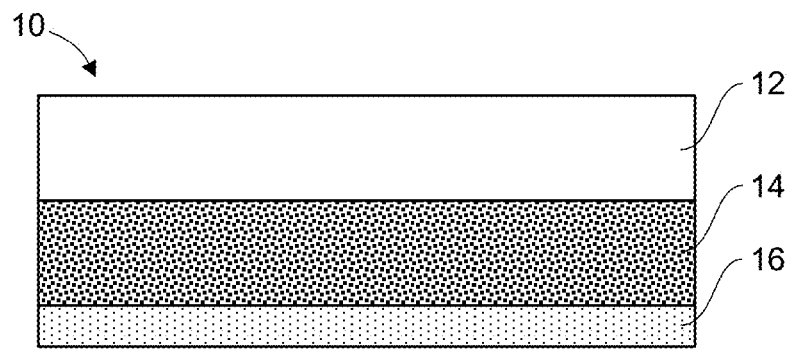
FIG. 1 is an illustration of a transdermal patch having a composite backing, an agent adhesive layer and a backing layer in accord with embodiments described herein.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

It is to be understood that, unless otherwise indicated, these aspects and embodiments are not limited to specific polymers, oligomers, crosslinking agents, additives, manufacturing processes, or adhesive products. It is also to be understood that the terminology used herein is for the purpose of describing particular embodiments only, and is not intended to be limiting.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The use of terms of order or importance, including "first" and "second", is to distinguish and identify individual elements and does not denote or imply a particular order or importance unless clearly indicated by context.

The term "active agent" as used herein refers to a chemical material or compound suitable for topical or transdermal administration and that induces a desired effect. The terms include agents that are therapeutically effective, prophylactically effective, and cosmetically effective agents. The terms "active agent", "drug" and "therapeutic agent" are used interchangeably herein.

The term "hydrogel" is used in the conventional sense to refer to water-swellable polymeric matrices that can absorb a substantial amount of water to form elastic gels, wherein "matrices" are three-dimensional networks of macromolecules held together by covalent or noncovalent crosslinks. Upon placement in an aqueous environment, dry hydrogels swell to the extent allowed by the degree of cross-linking.

The term "hydrogel composition" refers to a composition that either contains a hydrogel or is entirely composed of a hydrogel. As such, "hydrogel compositions" encompass not only hydrogels per se but also compositions that not only contain a hydrogel but also contain one or more non-hydrogel components or compositions, e.g., hydrocolloids, which contain a hydrophilic component (which may contain or be a hydrogel) distributed in a hydrophobic phase.

"Matrix" as used herein refers to a solid or semi-solid substance including, but not limited to, a polymeric material, adhesive or gel. The matrix typically serves as a repository or carrier for substances including the therapeutic agent.

"Occlusive" as used herein refers to a material that limits the diffusion rate of moisture vapor and/or oxygen. A "non-occlusive" material allows a higher diffusion rate for moisture vapor and/or oxygen.

"Optional" or "optionally" means that the subsequently described circumstance may or may not occur, so that the description includes instances where the circumstance occurs and instances where it does not.

The term "skin" as used herein refers to skin or other biological membranes or mucosal tissue, including the interior surface of body cavities that have a mucosal lining. The term "skin" should be interpreted as including "mucosal tissue" and vice versa. It will be understood by persons of skill in the art that in most or all instances the same inventive principles apply to administration through other biological membranes such as those which line the interior of the mouth (e.g. oral mucosal membranes), gastro-intestinal tract, blood-brain barrier, or other body tissues or organs or biological membranes which are exposed or accessible during surgery or during procedures such as laparoscopy or endoscopy.

"Substantially" or "essentially" means nearly totally or completely, for instance, 90-95% or greater of some given quantity.

The term "therapeutically effective amount" as used herein refers to the amount of an active agent that is nontoxic but sufficient to provide the desired therapeutic effect. The amount that is "effective" will vary from subject to subject, depending on the age and general condition of the individual, the particular active agent or agents, and the like as known to those skilled in the art.

The terms "transdermal" or "transdermal delivery" as used herein refer to administration of an active agent to a body surface of an individual so that the agent passes through the body surface, e.g., skin, and into the individual's blood stream (systemic circulation). The term "transdermal" is intended to include transmucosal administration, i.e., administration of a drug to the mucosal (e.g., sublingual, buccal, vaginal, rectal) surface of an individual so that the agent passes through the mucosal tissue and into the individual's blood stream.

The terms "transdermal patch", "transdermal device" and/or "transdermal system" all relate to a layered patch, device or system that provides transdermal delivery of an active agent therefrom. The terms are used interchangeably herein.

II. Transdermal Devices and Systems

The systems and devices described herein are designed for prolonged or long term transdermal administration of an active agent. The compositions may be used in devices, patches or systems suitable for transdermal delivery of the active agent. Reference to a transdermal device, system or patch herein applies equally to each of the terms. The devices and systems are especially useful for long term delivery of the active agent from the device. For the long term delivery, the system must remain adhered or substantially adhered to the administration site as delivery of the active agent from the transdermal device requires contact between the agent containing layer and the administration site (directly or indirectly). Most transdermal patches cannot or do not remain sufficiently adhered to the skin for an extended period of more than a couple of days. Many commercial patches advise users to replace patches that peel off the skin or become substantially unadhered. The adhesion problem becomes greater for larger patch sizes and/or for patches that are applied for longer durations such as more than 1-3 days. Friction between moving skin and the static backing layer increases shear resistance of the adhesive/drug layer that is adhered to the stiff backing layer. These patches are either lifted off the skin or become buckled up from the skin, causing the patch to lose contact with the skin. Eventually, this results in patch failure. This friction may also lead to skin irritation, particularly along the edges of the patch. The propensity for larger patches to buckle or fail practically limits the size of patches. Because the patch size is one factor in the dose of the active agent that is delivered, the patch size may also limit the dose and duration of administration of the active agent.

In some embodiments, the present transdermal devices and systems provide a transdermal device or system that includes a composite backing layer that reduces friction within the device or system and allows for long term wear, larger patch size, and/or reduced skin irritation. In some embodiments, the present transdermal devices and systems provide a transdermal device or system that includes at least one layer that is at least partially segmented or divided. In some embodiments, the transdermal device or system includes at least one internal patch layer that is at least partially segmented or divided, which reduces friction within the device or system and allows for long term wear, larger patch size, and/or reduced skin irritation.

In some embodiments, the transdermal device, patch or system is useful for long term or extended wear or administration. In embodiments, the transdermal device is suitable for administration of at least about 3 days or more. In some embodiments, the transdermal device is suitable for administration of at least about or up to about 3-14 days. In some embodiments, the transdermal device is suitable for administration up to about 10-14 days. In some embodiments, the transdermal device is suitable for administration of at least about or up to about 3-5 days, 3-7 days, 3-10 days, 5-7 days, 5-10 days, 5-14 days, 6-10 days, 6-14 days, 7-10 days, 7-14 days, 8-10 days, 8-14 days, 9-10 days, 9-14 days, or 10-14 days. In some non-limiting embodiments, the transdermal device is suitable for administration of at least about or up to about 3 days, 4 days, 5 days, 6 days, 7 days, 8 days, 9 days, 10 days, or 14 days. By suitable for administration, it is meant that the device, patch or system remains sufficiently adhered to the administration site to allow for contact of the adhesive drug layer with the skin such that the active agent is transdermally delivered. In embodiments, the device, patch or system is continuously adhered to the administration site. In some embodiments, the device, patch or system is substantially adhered to the administration site.

FIG. 1 shows an embodiment of an exemplary transdermal patch, device or system, generally designated at 10, having a composite backing layer or overlay. In this embodiment, the device includes a composite backing layer 12, an adhesive drug layer 14 and an optional release liner 16.

The backing layer provides a structural element for holding or supporting the adhesive drug layer. In the discussion of the backing layer below, it will be appreciated that the discussion applies to the backing layer as a whole as well as any one or more of the individual layers of the composite backing layer. The backing layer may be formed of any suitable material as known in the art. In some embodiments, the backing layer is occlusive or breathable. In some embodiments, the backing layer is preferably impermeable or substantially impermeable to moisture by preventing passage of all or substantially all moisture. In one exemplary embodiment, the barrier layer has an MVTR (moisture vapor transmission rate) of less than about 50 g/m$^2$/day. In some embodiments, the barrier layer has an MVTR of about 0.5-1500 g/m$^2$/day or about 0.5-50 g/m$^2$/day. In some specific but not limiting embodiments, the barrier layer has an MVTR of less than about or about 0.5 g/m$^2$/day, 1 g/m$^2$/day, 5 g/m$^2$/day, 10 g/m$^2$/day, 15 g/m$^2$/day, 20 g/m$^2$/day, 25 g/m$^2$/day, 30 g/m$^2$/day, 40 g/m$^2$/day, or 50 g/m$^2$/day. In some embodiments, the backing layer is preferably inert and/or does not absorb components of the adhesive drug layer, including the active agent. In some embodiments, the backing layer preferably prevents release of components of the adhesive drug layer through the backing layer. The backing layer may be flexible, substantially flexible or nonflexible. The backing layer is preferably at least partially flexible such that the backing layer is able to conform at least partially to the shape of the skin where the patch is applied. In some embodiments, the backing layer is flexible such that the backing layer conforms to the shape of the skin where the patch is applied. In some embodiments, the backing layer is sufficiently flexible to maintain contact at the application site with movement, e.g. skin movement. Typically, at least some of the materials used for the backing layer should permit the device to follow the contours of the skin or other application site and be worn comfortably on areas of skin such as at joints or other points of flexure, that are normally subjected to mechanical strain with little or no likelihood of the device disengaging from the skin due to differences in the flexibility or resiliency of the skin and the device. In some embodiments, the backing layer does not affect and/or control the release profile of the active agent from the device. In some embodiments, the backing layer is not the predominant factor affecting and/or controlling the release profile of the active agent from the device.

In some embodiments, at least a portion of the transdermal patch has a size or surface area of about 5-200 cm$^2$. In some non-limiting embodiments, the transdermal patch has a size or surface area of about 5-10 cm$^2$, 5-15 cm$^2$, 5-20 cm$^2$, 5-25 cm$^2$, 5-30 cm$^2$, 5-40 cm$^2$, 5-45 cm$^2$, 5-50 cm$^2$, 5-60 cm$^2$, 5-70 cm$^2$, 5-75 cm$^2$, 5-80 cm$^2$, 5-90 cm$^2$, 5-100 cm$^2$, 5-125 cm$^2$, 5-150 cm$^2$, 5-175 cm$^2$, 10-15 cm$^2$, 10-20 cm$^2$, 10-25 cm$^2$, 10-30 cm$^2$, 10-40 cm$^2$, 10-45 cm$^2$, 10-50 cm$^2$, 10-60 cm$^2$, 10-70 cm$^2$, 10-75 cm$^2$, 10-80 cm$^2$, 10-90 cm$^2$, 10-100 cm$^2$, 10-125 cm$^2$, 10-150 cm$^2$, 10-175 cm$^2$, 10-200 cm$^2$, 15-20 cm$^2$, 15-25 cm$^2$, 15-30 cm$^2$, 15-40 cm$^2$, 15-45 cm$^2$, 15-50 cm$^2$, 15-60 cm$^2$, 15-70 cm$^2$, 15-75 cm$^2$, 15-80 cm$^2$, 15-90 cm$^2$, 15-100 cm$^2$, 15-125 cm$^2$, 15-150 cm$^2$, 15-175 cm$^2$, 15-200 cm$^2$, 20-25 cm$^2$, 20-30 cm$^2$, 20-40 cm$^2$, 20-45 cm$^2$, 20-50 cm$^2$, 25-60 cm$^2$, 25-70 cm$^2$, 25-75 cm$^2$, 25-80 cm$^2$, 25-90 cm$^2$, 25-100 cm$^2$, 25-125 cm$^2$, 25-150 cm$^2$, 25-175 cm$^2$, 25-200 cm$^2$, 25-30 cm$^2$, 25-40 cm$^2$, 25-45 cm$^2$, 25-50 cm$^2$, 25-60 cm$^2$, 25-70 cm$^2$, 25-75 cm$^2$, 25-80 cm$^2$, 25-90 cm$^2$, 25-100 cm$^2$, 25-125 cm$^2$, 25-150 cm$^2$, 25-175 cm$^2$, 25-200 cm$^2$, 30-40 cm$^2$, 30-45 cm$^2$, 30-50 cm$^2$, 30-60 cm$^2$, 30-70 cm$^2$, 30-75 cm$^2$, 30-80 cm$^2$, 30-90 cm$^2$, 30-100 cm$^2$, 30-125 cm$^2$, 30-150 cm$^2$, 30-175 cm$^2$, 30-200 cm$^2$, 40-45 cm$^2$, 40-50 cm$^2$, 40-60 cm$^2$, 40-70 cm$^2$, 40-75 cm$^2$, 40-80 cm$^2$, 40-90 cm$^2$, 40-100 cm$^2$, 40-125 cm$^2$, 40-150 cm$^2$, 40-175 cm$^2$, 40-200 cm$^2$, 45-50 cm$^2$, 45-60 cm$^2$, 45-70 cm$^2$, 45-75 cm$^2$, 45-80 cm$^2$, 45-90 cm$^2$, 45-100 cm$^2$, 45-125 cm$^2$, 45-150 cm$^2$, 45-175 cm$^2$, 45-200 cm$^2$, 50-60 cm$^2$, 50-70 cm$^2$, 50-75 cm$^2$, 50-80 cm$^2$, 50-90 cm$^2$, 50-100 cm$^2$, 50-125 cm$^2$, 50-150 cm$^2$, 50-175 cm$^2$, 50-200 cm$^2$, 60-70 cm$^2$, 60-75 cm$^2$, 60-80 cm$^2$, 60-90 cm$^2$, 60-100 cm$^2$, 60-125 cm$^2$, 60-150 cm$^2$, 60-175 cm$^2$, 60-200 cm$^2$, 70-75 cm$^2$, 70-80 cm$^2$, 70-90 cm$^2$, 70-100 cm$^2$, 70-125 cm$^2$, 70-150 cm$^2$, 70-175 cm$^2$, 70-200 cm$^2$, 80-90 cm$^2$, 80-100 cm$^2$, 80-125 cm$^2$, 80-150 cm$^2$, 80-175 cm$^2$, 80-200 cm$^2$, 90-100 cm$^2$, 90-125 cm$^2$, 90-150 cm$^2$, 90-175 cm$^2$, 90-200 cm$^2$, 100-125 cm$^2$, 100-150 cm$^2$, 100-175 cm$^2$, 100-200 cm$^2$, 125-150 cm$^2$, 125-175 cm$^2$, 125-200 cm$^2$, 150-175 cm$^2$, 150-200 cm$^2$, or 175-200 cm$^2$. In specific, but not limiting, embodiments, the transdermal patch has a size or surface area of about 5 cm$^2$, 10 cm$^2$, 15 cm$^2$, 20 cm$^2$, 25 cm$^2$, 30 cm$^2$, 40 cm$^2$, 45 cm$^2$, 50 cm$^2$, 60 cm$^2$, 70 cm$^2$, 75 cm$^2$, 80 cm$^2$, 90 cm$^2$, 100 cm$^2$, 125 cm$^2$, 150 cm$^2$, 175 cm$^2$, or 200 cm$^2$. It will be appreciated that different layers of the backing and/or the device may have a different surface area or size. in one embodiment, at least a portion (e.g. at least one layer) of the backing extends beyond the edge of at least the adhesive drug layer.

The transdermal patch may be prepared to have a thickness such that the desired amount of drug formulation is contained within the patch including the desired components while maintaining a thickness that is wearable and comfortable for the subject. In some embodiments, the transdermal patch has a thickness of about 2-200 mil including the composite backing layer and the adhesive drug layer. In specific non-limiting embodiments, the transdermal patch has a thickness of about 2-10 mil, 2-25 mil, 2-30 mil, 2-40 mil, 2-50 mil, 2-75 mil, 2-80 mil, 2-100 mil, 2-125 mil, 2-150 mil, 2-175 mil, 2.5-10 mil, 2.5-25 mil, 2.5-30 mil, 2.5-40 mil, 2.5-50 mil, 2.5-75 mil, 2.5-80 mil, 2.5-100 mil, 2.5-125 mil, 2.5-150 mil, 2.5-175 mil, 2.5-200 mil, 3-10 mil, 3-25 mil, 3-30 mil, 3-40 mil, 3-50 mil, 3-75 mil, 3-80 mil, 3-100 mil, 3-125 mil, 3-150 mil, 3-175 mil, 3-200 mil, 5-10 mil, 5-25 mil, 5-30 mil, 5-40 mil, 5-50 mil, 5-75 mil, 5-80 mil, 5-100 mil, 5-125 mil, 5-150 mil, 5-175 mil, 5-200 mil, 7-10 mil, 7-25 mil, 7-30 mil, 7-40 mil, 7-50 mil, 7-75 mil, 7-80 mil, 7-100 mil, 7-125 mil, 7-150 mil, 7-175 mil, 7-200 mil, 8-10 mil, 8-25 mil, 8-30 mil, 8-40 mil, 8-50 mil, 8-75 mil, 8-80 mil, 8-100 mil, 8-125 mil, 8-150 mil, 8-175 mil, 8-200 mil, 10-25 mil, 10-30 mil, 10-40 mil, 10-50 mil, 10-75 mil, 10-80 mil, 10-100 mil, 10-125 mil, 10-150 mil, 10-175 mil, 10-200 mil, 25-30 mil, 25-40 mil, 25-50 mil, 25-75 mil, 25-80 mil, 25-100 mil, 25-125 mil, 25-150 mil, 25-175 mil, 25-200 mil, 30-40 mil, 30-50 mil, 30-75 mil, 30-80 mil, 30-100 mil, 30-125 mil, 30-150 mil, 30-175 mil, 30-200 mil, 40-50 mil, 40-75 mil, 40-80 mil, 40-100 mil, 40-125 mil, 40-150 mil, 40-175 mil, 40-200 mil, 50-75 mil, 50-80 mil, 50-100 mil, 50-125 mil, 50-150 mil, 50-175 mil, 50-200 mil, 75-80 mil, 75-100 mil, 75-125 mil, 75-150 mil, 75-175 mil, 75-200 mil, 80-100 mil, 80-125 mil, 80-150 mil, 80-175 mil, 80-200 mil, 100-125 mil, 100-150 mil, 100-175 mil, 100-200 mil, 125-150 mil, 125-175 mil, 125-200 mil, 150-175 mil, 150-200 mil, or 175-200 mil. In specific, but not limiting, embodiments, the transdermal patch has a thickness of about 2 mil, 2.5 mil, 3 mil, 4 mil, 5 mil, 7 mil, 7.5 mil, 8 mil, 10 mil, 15 mil, 20 mil, 25 mil, 30 mil, 40 mil, 50 mil, 60 mil, 70 mil, 75 mil, 80 mil, 90 mil, 100 mil, 125 mil, 150 mil, 175 mil, or 200 mil. The thickness for the patch describes above may apply to the patch including the optional release liner or the patch as applied (including only the backing and drug layers).

Figure 2:
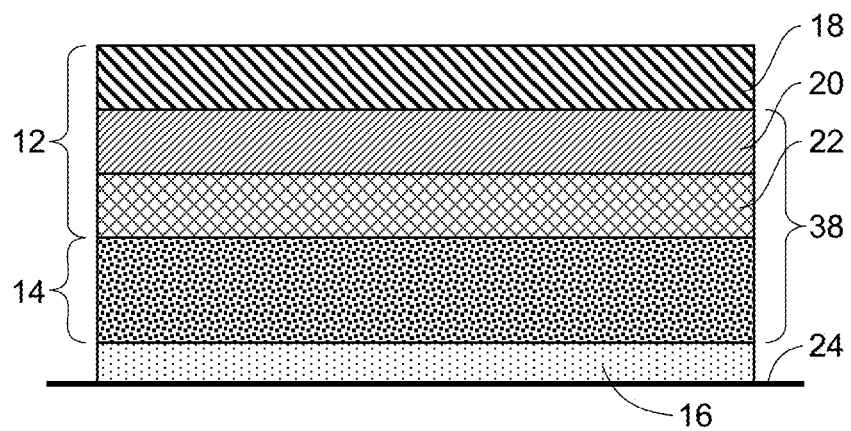
FIG. 2 is an illustration of a transdermal patch comprising a layered composite backing in accord with embodiments described herein.
Figure 3:
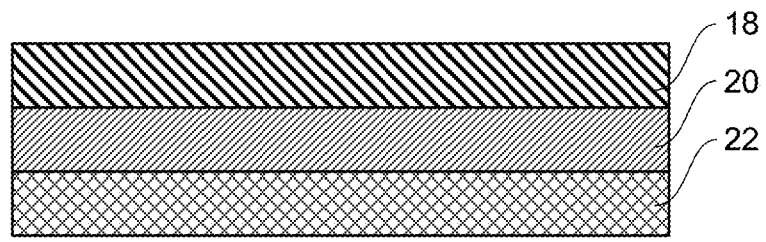
FIG. 3 is an illustration of a composite backing in accord with embodiments described herein.

In a first aspect, as seen in FIGS. 2 and 3, the backing layer or overlay 12 is a composite comprising multiple or several layers to allow movement within the composite backing/and or the adhesive drug layer 14. The composite layers may be laminated or otherwise adhered as known in the art. Lamination generally refers to manufacture by layering and adhering materials. In embodiments as shown in FIG. 3, the backing layer comprises a first exterior or top layer 18, a second, middle layer 20, and a third or bottom layer 22. In the embodiment as shown in FIG. 2, at least the second/middle layer 20 and the third/bottom layer 22 of the composite backing as well as the adhesive/drug layer 14, collectively indicated at 38, allow for shear yield and/or movement to allow dissipation of movement within the transdermal delivery system. In other embodiments, at least the first/top layer 18 and the second/middle layer 20 of the composite backing allow for shear yield and/or movement to allow dissipation of movement within the transdermal delivery system.

In non-limiting embodiments, the composite layer has a thickness of about 2-100 mil. In specific non-limiting embodiments, the composite layer has a thickness of about 5-10 mil, 5-15 mil, 5-20 mil, 5-25 mil, 5-30 mil, 5-40 mil, 5-50 mil, 5-60 mil, 5-70 mil, 5-75 mil, 5-80 mil, 5-90 mil, 5-100 mil, 10-15 mil, 10-20 mil, 10-25 mil, 10-30 mil, 10-40 mil, 10-50 mil, 10-60 mil, 10-70 mil, 10-75 mil, 10-80 mil, 10-90 mil, 10-100 mil, 15-20 mil, 15-25 mil, 15-30 mil, 15-40 mil, 15-50 mil, 15-60 mil, 15-70 mil, 15-75 mil, 15-80 mil, 15-90 mil, 15-100 mil, 20-25 mil, 20-30 mil, 20-40 mil, 20-50 mil, 20-60 mil, 20-70 mil, 20-75 mil, 20-80 mil, 20-90 mil, 20-100 mil, 25-30 mil, 25-40 mil, 25-50 mil, 25-60 mil, 25-70 mil, 25-75 mil, 25-80 mil, 25-90 mil, 25-100 mil, 30-40 mil, 30-50 mil, 30-60 mil, 30-70 mil, 30-75 mil, 30-80 mil, 30-90 mil, 30-100 mil, 40-50 mil, 40-60 mil, 40-70 mil, 40-75 mil, 40-80 mil, 40-90 mil, 40-100 mil, 50-60 mil, 50-70 mil, 50-75 mil, 50-80 mil, 50-90 mil, 50-100 mil, 50-70 mil, 50-75 mil, 50-80 mil, 50-90 mil, 50-100 mil, 60-70 mil, 60-75 mil, 60-80 mil, 60-90 mil, 60-100 mil, 70-75 mil, 70-80 mil, 70-90 mil, 70-100 mil, 75-80 mil, 75-90 mil, 75-100 mil, 80-90 mil, 80-100 mil, or 90-100 mil.

The first layer is a protective outer layer which serves at least to protect the patch. In some embodiments, the first layer overlays or overhangs at least one edge of at least one of the second layer, third layer, or the adhesive/drug layer. In embodiments, the first layer is comprised of a woven or non-woven fabric, a woven or non-woven polymer fabric, a polymer film, which may be elastic, an occlusive polymer film, a polymer laminate and a polymer/metal laminate. A woven fabric is generally produced from warp and weft polymeric or natural fibers. Exemplary woven or non-woven fabrics are polyester fabrics. One exemplary woven fabric is a bi-elastic polyester fabric such as the KOB 053 available from Karl Otto GmbH & Co. In some embodiments, the polymer film is an elastic polymer film.

In some embodiments, the first layer is comprised of one or more stretchable polymers. In some embodiments, the first layer is comprised of one or more polymers having a low shear strength or resistance. The shear strength may be measured by any methods as known in the art. Some exemplary methods of testing or measuring shear strength include the punch technique or test and the losipescu test as known to those skilled in the art. In some embodiments, the shear strength may be measured using a viscometer.

In some embodiments, the shear strength is expressed in terms of a percentage of the tensile strength of the polymer(s). In some non-limiting embodiments, one or more of the polymers of the second layer have a shear strength that is or is less than about 1-25% of its tensile strength. In some embodiments, one or more of the polymers has a shear strength that is or is less than about 1-20%, 1-15%, 1-10%, 1-5%, 5-25%, 5-20%, 5-15%, 5-10%, 10-25%, 10-20%, 10-15%, 15-25%, 15-20%, or 20-25% of the tensile strength for the polymer. In some specific, but not limiting embodiments, one or more of the polymers has a shear strength that is or is less than about 1%, 5%, 10%, 15%, 20%, 25%, 30%, or 40% of the tensile strength for the polymer. In some embodiments, the shear strength is about or less than about 0.1-15 MPa. In some embodiments, the shear strength is about or less than about 0.1-10 MPa, 0.1-9 MPa, 0.1-8 MPa, 0.1-7 MPa, 0.1-6 MPa, 0.1-5 MPa, 0.1-4 MPa, 0.1-3 MPa, 0.1-2 MPa, 0.1-1 MPa, 0.1-0.5 MPa, 0.5-15 MPa, 0.5-10 MPa, 0.5-9 MPa, 0.5-8 MPa, 0.5-7 MPa, 0.5-6 MPa, 0.5-5 MPa, 0.5-4 MPa, 0.5-3 MPa, 0.5-2 MPa, 0.5-1 MPa, 1-15 MPa, 1-10 MPa, 1-9 MPa, 1-8 MPa, 1-7 MPa, 1-6 MPa, 1-5 MPa, 1-4 MPa, 1-3 MPa, 1-2 MPa, 2-15 MPa, 2-10 MPa, 2-9 MPa, 2-8 MPa; 2-7 MPa, 2-6 MPa, 2-5 MPa, 2-4 MPa, 2-3 MPa, 3-15 MPa, 3-10 MPa, 3-9 MPa, 3-8 MPa, 3-7 MPa, 3-6 MPa, 3-5 MPa, 3-4 MPa, 4-15 MPa, 4-10 MPa, 4-9 MPa, 4-8 MPa, 4-7 MPa, 4-6 MPa, 4-5 MPa, 5-15 MPa, 5-10 MPa, 5-9 MPa, 5-8 MPa, 5-7 MPa, 5-6 MPa, 6-15 MPa, 6-10 MPa, 6-9 MPa, 6-8 MPa, 6-7 MPa, 7-15 MPa, 7-10 MPa, 7-9 MPa, 7-8 MPa, 8-15 MPa, 8-10 MPa, 8-9 MPa, 9-15 MPa, 9-10 MPa, or 10-15 MPa.

Suitable polymers are known in the art and include elastomers, polyesters, polyethylenes, polypropylenes, polyurethanes, polyether amides and copolymers thereof. In some embodiments, the polymer is polyethylene vinyl acetate, polyvinylchloride or copolymers thereof. In some embodiments, the first layer is comprised of one or more of polyethylene terephthalate, polyvinyl acetate, polyvinylidene chloride, polyvinylchloride, and polyethylene vinyl acetate or copolymers thereof. Polymer/metal laminates are known in the art and include aluminum laminates and tin laminates, among others. In some embodiments, the first layer is comprised of a laminate. In one non-limiting embodiment, the first layer is comprised of a polyethylene and polyester laminate such as the laminate sold under the name Scotchpak™ #9723. In some embodiments, the first layer is formed of a polyurethane film, a thermoplastic polyester elastomer such as a Hytrel® film available from DuPont®, or a polyethylene vinyl acetate film. In some embodiments, at least the first layer of the backing layer is occlusive.

In some embodiments, the first layer is a stretchable, elastic and/or flexible layer comprised of one or more polymers having a stretchability and/or elasticity of at least about 5% in at least one direction. In this embodiment, the first layer, along with the second or middle layer absorbs the stress of the movement of the adhesive drug layer or device against the skin or other administration site. In some embodiments, the first layer is comprised of one or more stretchable polymers having a stretchability and/or elasticity of at least about 5% or at least about 10% in at least one direction. The stretchability may be ascertained by any suitable means as known in the art. In some embodiments, the stretchability is determined at room temperature or at approximately 20-25° C. In embodiments, the first layer is comprised of one or more stretchable polymers having a stretchability and/or elasticity of at least about 5-50%. In some embodiments, the first layer is comprised of one or more stretchable polymers having a stretchability and/or elasticity of at least about 5-40%, 5-30%, 5-25%, 5-20%, 5-15%, 5-10%, 10-50%, 10-40%, 10-30%, 10-25%, 10-20%, 10-15%, 15-50%, 15-40%, 15-30%, 15-25%, 15-20%, 20-50%, 20-40%, 20-30%, 20-25%, 25-50%, 25-40%, 25-30%, 30-50%, 30-40%, or 40-50%. In specific, but not limiting embodiments, the first layer is comprised of one or more stretchable polymers having a stretchability and/or elasticity of at least about 5%, 10%, 15%, 20%, 25%, 30%, 40%, or 50%. In some embodiments, the first layer is stretchable, but not elastic. In other embodiments, the first layer is relatively stiff.

In embodiments, the first layer has a thickness of about 0.2-50 mil. In non-limiting embodiments, the first layer has a thickness of between about 0.2-0.5 mil, 0.2-1 mil, 0.2-1.5 mil, 0.2-2 mil, 0.2-5 mil, 0.2-10 mil, 0.2-15 mil, 0.2-20 mil, 0.2-25 mil, 0.2-30 mil, 0.2-35 mil, 0.2-40 mil, 0.2-45 mil, 0.5-0.75 mil, 0.5-1 mil, 0.5-1.5 mil, 0.5-2 mil, 0.5-2.5 mil, 0.5-3 mil, 0.5-4 mil, 0.5-5 mil, 0.5-6 mil, 0.5-7 mil, 0.5-8 mil, 0.5-9 mil, 0.5-10 mil, 0.5-15 mil, 0.5-20 mil, 0.5-25 mil, 0.5-30 mil, 0.5-35 mil, 0.5-40 mil, 0.5-45 mil, 0.5-50 mil, 0.75-1 mil, 0.75-1.5 mil, 0.75-2 mil, 0.75-2.5 mil, 0.75-3 mil, 0.75-4 mil, 0.75-5 mil, 0.75-6 mil, 0.75-7 mil, 0.75-8 mil, 0.75-9 mil, 0.75-10 mil, 0.75-15 mil, 0.75-20 mil, 0.75-25 mil, 0.75-30 mil, 0.75-35 mil, 0.75-40 mil, 0.75-45 mil, 0.75-50 mil, 1-1.5 mil, 1-2 mil, 1-2.5 mil, 1-3 mil, 1-4 mil, 1-5 mil, 1-6 mil, 1-7 mil, 1-8 mil, 1-9 mil, 1-10 mil, 1-15 mil, 1-20 mil, 1-25 mil, 1-30 mil, 1-35 mil, 1-40 mil, 1-45 mil, 1-50 mil, 1.5-2 mil, 1.5-2.5 mil, 1.5-3 mil, 1.5-4 mil, 1.5-5 mil, 1.5-6 mil, 1.5-7 mil, 1.5-8 mil, 1.5-9 mil, 1.5-10 mil, 1.5-15 mil, 1.5-20 mil, 1.5-25 mil, 1.5-30 mil, 1.5-35 mil, 1.5-40 mil, 1.5-45 mil, 1.5-50 mil, 2-2.5 mil, 2-3 mil, 2-4 mil, 2-5 mil, 2-6 mil, 2-7 mil, 2-8 mil, 2-9 mil, 2-10 mil, 2-15 mil, 2-20 mil, 2-25 mil, 2-30 mil, 2-35 mil, 2-40 mil, 2-45 mil, 2-50 mil, 2.5-3 mil, 2.5-4 mil, 2.5-5 mil, 2.5-6 mil, 2.5-7 mil, 2.5-8 mil, 2.5-9 mil, 2.5-10 mil, 2.5-15 mil, 2.5-20 mil, 2.5-25 mil, 2.5-30 mil, 2.5-35 mil, 2.5-40 mil, 2.5-45 mil, 2.5-50 mil, 3-4 mil, 3-5 mil, 3-6 mil, 3-7 mil, 3-8 mil, 3-9 mil, 3-10 mil, 3-15 mil, 3-20 mil, 3-25 mil, 3-30 mil, 3-35 mil, 3-40 mil, 3-45 mil, 3-50 mil, 4-5 mil, 4-6 mil, 4-7 mil, 4-8 mil, 4-9 mil, 4-10 mil, 4-15 mil, 4-20 mil, 4-25 mil, 4-30 mil, 4-35 mil, 4-40 mil, 4-45 mil, 4-50 mil, 5-6 mil, 5-7 mil, 5-8 mil, 5-9 mil, 5-10 mil, 5-15 mil, 5-20 mil, 5-25 mil, 5-30 mil, 5-35 mil, 5-40 mil, 5-45 mil, 5-50 mil, 6-7 mil, 6-8 mil, 6-9 mil, 6-10 mil, 6-15 mil, 6-20 mil, 6-25 mil, 6-30 mil, 6-35 mil, 6-40 mil, 6-45 mil, 6-50 mil, 7-8 mil, 7-9 mil, 7-10 mil, 7-15 mil, 7-20 mil, 7-25 mil, 7-30 mil, 7-35 mil, 7-40 mil, 7-45 mil, 7-50 mil, 8-9 mil, 8-10 mil, 8-15 mil, 8-20 mil, 1-25 mil, 8-30 mil, 8-35 mil, 8-40 mil, 8-45 mil, 8-50 mil, 9-10 mil, 9-15 mil, 9-20 mil, 10-15 mil, 10-20 mil, 10-25 mil, 10-30 mil, 10-35 mil, 10-40 mil, 10-45 mil, 10-50 mil, 20-25 mil, 20-30 mil, 20-35 mil, 20-40 mil, 20-45 mil, 20-50 mil, 25-30 mil, 25-35 mil, 25-40 mil, 25-45 mil, 25-50 mil, 30-35 mil, 30-40 mil, 30-45 mil, 30-50 mil, 35-40 mil, 35-45 mil, 35-50 mil, 40-45 mil, 40-50 mil, or 45-50 mil. In specific non-limiting embodiments, the first layer has a thickness of about 0.5 mil, 0.75 mil, 1 mil, 1.5 mil, 2 mil, 3 mil, 4 mil, 5 mil, 6 mil, 7 mil, 8 mil, 9 mil, 10 mil, 15 mil, or 20 mil.

The composite backing layer further comprises a second or middle layer 20 adjacent the first or top layer. The second layer is preferably an adhesive, tie or binding layer positioned between the first and third layers. The second layer serves to adhere, attach or bind the first and third layers. In some embodiments, one of the first or third layers may be relatively stiff and/or stationary and the other of the first and third layer may be flexible and/or elastic. The second layer, along with the flexible or relatively flexible layer absorbs the stress of the adhesive drug layer against the skin or other administration site. In embodiments, the second layer is comprised of polymers having a tensile or yield strength of less than about 5 MPa or about 10 MPa. The tensile strength is a measurement of the force required per unit area (MPa) at the break point of the polymer. In some embodiments, the second layer is comprised of one or more polymers having a tensile strength of less than about 5-10 MPa. In some embodiments, the second layer is comprised of one or more polymers having a tensile strength of less than about 6-10 MPa, 7-10 MPa, 8-10 MPa, or 9-10 MPa. In some embodiments, the second layer is comprised of polymers such that the second layer as a whole has a tensile strength of less than about 10 MPa. The tensile or yield strength may be ascertained by any suitable means as known in the art. In one embodiment, the tensile or yield strength is determined by the ASTM D882 test which comprising pulling a polymer sample from both ends to determine the force required at the yield or break point. In some embodiments, the tensile strength is the tensile strength at room temperature or at approximately 20-25° C. In embodiments, the second layer is comprised of polymers having an elongation of not less than or at least about 10%. In some embodiments, the second layer is comprised of polymers having an elongation of not less than or at least about 50%. The elongation refers to the percentage of elongation before the polymer breaks under an applied strain. In embodiments, the % elongation is the final length (L) of the polymer or polymer material after stretching, minus the initial length ($L_i$) divided by the initial length. The % elongation may be ascertained by any suitable means as known in the art. In some embodiments, the % elongation is determined at room temperature or at approximately 20-25° C. In some embodiments, the second layer is comprised of polymers such that the second layer as a whole has a % elongation of at least about or not less than about 10% or about 50%. In some embodiments, the second layer is comprised of one or more polymers having a % elongation of at least about 10-500%. In some embodiments, the second layer is comprised of one or more polymers having a % elongation of at least about 10-75%, 10-100%, 10-150%, 10-200%, 10-250%, 10-300%, 10-400%, 50-75%, 50-100%, 50-150%, 50-200%, 50-250%, 50-300%, 50-400%, 50-500%, 75-100%, 75-150%, 75-200%, 75-250%, 75-300%, 75-400%, 75-500%, 100-150%, 100-200%, 100-250%, 100-300%, 100-400%, 100-500%, 150-200%, 150-250%, 150-300%, 150-400%, 150-500%, 200-250%, 200-300%, 200-400%, 200-500%, 250-300%, 250-400%, 250-500%, 300-400%, 300-500%, 400-500% or more.

In some embodiments, the second layer is comprised of one or more polymers having a low shear strength. Shear strength refers to the polymer's ability to resist forces that cause the internal structure to slide against itself. In some embodiments, the shear strength is expressed in terms of a percentage of the tensile strength of the polymer(s). In some non-limiting embodiments, one or more of the polymers of the second layer have a shear strength that is or is less than about 1-25% of its tensile strength. In some embodiments, one or more of the polymers has a shear strength that is or is less than about 1-20%, 1-15%, 1-10%, 1-5%, 5-25%, 5-20%, 5-15%, 5-10%, 10-25%, 10-20%, 10-15%, 15-25%, 15-20%, or 20-25% of the tensile strength for the polymer. In some specific, but not limiting embodiments, one or more of the polymers has a shear strength that is or is less than about 1%, 5%, 10%, 15%, 20%, 25%, 30%, or 40% of the tensile strength for the polymer. In some embodiments, the shear strength is about or less than about 0.1-15 MPa. In some embodiments, the shear strength is about or less than about 0.1-10 MPa, 0.1-9 MPa, 0.1-8 MPa, 0.1-7 MPa, 0.1-6 MPa, 0.1-5 MPa, 0.1-4 MPa, 0.1-3 MPa, 0.1-2 MPa, 0.1-1 MPa, 0.1-0.5 MPa, 0.5-15 MPa, 0.5-10 MPa, 0.5-9 MPa, 0.5-8 MPa, 0.5-7 MPa, 0.5-6 MPa, 0.5-5 MPa, 0.5-4 MPa, 0.5-3 MPa, 0.5-2 MPa, 0.5-1 MPa, 1-15 MPa, 1-10 MPa, 1-9 MPa, 1-8 MPa, 1-7 MPa, 1-6 MPa, 1-5 MPa, 1-4 MPa, 1-3 MPa, 1-2 MPa, 2-15 MPa, 2-10 MPa, 2-9 MPa, 2-8 MPa, 2-7 MPa, 2-6 MPa, 2-5 MPa, 2-4 MPa, 2-3 MPa, 3-15 MPa, 3-10 MPa, 3-9 MPa, 3-8 MPa, 3-7 MPa, 3-6 MPa, 3-5 MPa, 3-4 MPa, 4-15 MPa, 4-10 MPa, 4-9 MPa, 4-8 MPa, 4-7 MPa, 4-6 MPa, 4-5 MPa, 5-15 MPa, 5-10 MPa, 5-9 MPa, 5-8 MPa, 5-7 MPa, 5-6 MPa, 6-15 MPa, 6-10 MPa, 6-9 MPa, 6-8 MPa, 6-7 MPa, 7-15 MPa, 7-10 MPa, 7-9 MPa, 7-8 MPa, 8-15 MPa, 8-10 MPa, 8-9 MPa, 9-15 MPa, 9-10 MPa, or 10-15 MPa.

In embodiments, the one or more polymers are selected from acrylates and acrylate copolymers, polyisobutylenes, silicone, polystyrene butyl rubber, polyethylene vinyl acetate and copolymers thereof. In some embodiments, the second layer is comprised of an adhesive selected from acrylic adhesives, polyisobutylene adhesives, or silicone adhesives. In some embodiments, the adhesive is a pressure sensitive adhesive. In some embodiments, the second layer is comprised of plasticized polymers.

In embodiments, the second layer has a thickness of about 0.5-30 mil. In non-limiting embodiments, the second layer has a thickness of between about 0.5-0.75 mil, 0.5-1 mil, 0.5-1.5 mil, 0.5-2 mil, 0.5-2.5 mil, 0.5-3 mil, 0.5-4 mil, 0.5-5 mil, 0.5-6 mil, 0.5-7 mil, 0.5-8 mil, 0.5-9 mil, 0.5-10 mil, 0.5-15 mil, 0.5-20 mil, 0.5-25 mil, 0.75-1 mil, 0.75-1.5 mil, 0.75-2 mil, 0.75-2.5 mil, 0.75-3 mil, 0.75-4 mil, 0.75-5 mil, 0.75-6 mil, 0.75-7 mil, 0.75-8 mil, 0.75-9 mil, 0.75-10 mil, 0.75-15 mil, 0.75-20 mil, 0.75-25 mil, 0.75-30 mil, 1-1.5 mil, 1-2 mil, 1-2.5 mil, 1-3 mil, 1-4 mil, 1-5 mil, 1-6 mil, 1-7 mil, 1-8 mil, 1-9 mil, 1-10 mil, 1-15 mil, 1-20 mil, 1-25 mil, 1-30 mil, 1.5-2 mil, 1.5-2.5 mil, 1.5-3 mil, 1.5-4 mil, 1.5-5 mil, 1.5-6 mil, 1.5-7 mil, 1.5-8 mil, 1.5-9 mil, 1.5-10 mil, 1.5-15 mil, 1.5-20 mil, 1.5-25 mil, 1.5-30 mil, 2-2.5 mil, 2-3 mil, 2-4 mil, 2-5 mil, 2-6 mil, 2-7 mil, 2-8 mil, 2-9 mil, 2-10 mil, 2-15 mil, 2-20 mil, 2-25 mil, 2-30 mil, 2.5-3 mil, 2.5-4 mil, 2.5-5 mil, 2.5-6 mil, 2.5-7 mil, 2.5-8 mil, 2.5-9 mil, 2.5-10 mil, 2.5-15 mil, 2.5-20 mil, 2.5-25 mil, 2.5-30 mil, 3-4 mil, 3-5 mil, 3-6 mil, 3-7 mil, 3-8 mil, 3-9 mil, 3-10 mil, 3-15 mil, 3-20 mil, 3-25 mil, 3-30 mil, 4-5 mil, 4-6 mil, 4-7 mil, 4-8 mil, 4-9 mil, 4-10 mil, 4-15 mil, 4-20 mil, 4-25 mil, 4-30 mil, 5-4 mil, 5-5 mil, 5-6 mil, 5-7 mil, 5-8 mil, 5-9 mil, 5-10 mil, 5-15 mil, 5-20 mil, 5-25 mil, 5-30 mil, 6-7 mil, 6-8 mil, 6-9 mil, 6-10 mil, 6-15 mil, 6-20 mil, 6-25 mil, 6-30 mil, 7-8 mil, 7-9 mil, 7-10 mil, 7-15 mil, 7-20 mil, 7-25 mil, 7-30 mil, 8-9 mil, 8-10 mil, 8-15 mil, 8-20 mil, 8-25 mil, 8-30 mil, 9-10 mil, 9-15 mil, 9-20 mil, 9-25 mil, 9-30 mil, 10-15 mil, 10-20 mil, 10-25 mil, 10-30 mil, 15-20 mil, 15-25 mil, 15-30 mil, 20-25 mil, 20-30 mil, or 25-30 mil. In specific non-limiting embodiments, the second layer has a thickness of about 0.5 mil, 0.75 mil, 1 mil, 1.5 mil, 2 mil, 3 mil, 4 mil, 5 mil, 6 mil, 7 mil, 8 mil, 9 mil, 10 mil, 15 mil, 20 mil, 25 mil, or 30 mil.

The composite backing layer further comprises a third or bottom layer adjacent the second or middle layer. In some embodiments, the third layer is a stretchable and/or flexible layer. In embodiments, the third layer, along with the second or middle layer absorbs the stress of the movement of the adhesive drug layer against the skin or other administration site. In some embodiments, the third layer is comprised of one or more stretchable polymers having a stretchability and/or elasticity of at least about 5% or at least about 10% in at least one direction. The stretchability may be ascertained by any suitable means as known in the art. In some embodiments, the stretchability is determined at room temperature or at approximately 20-25° C. In embodiments, the third layer is comprised of one or more stretchable polymers having a stretchability or elasticity of at least about 5-50%. In some embodiments, the third layer is comprised of one or more stretchable polymers having a stretchability or elasticity of at least about 5-40%, 5-30%, 5-25%, 5-20%, 5-15%, 5-10%, 10-50%, 10-40%, 10-30%, 10-25%, 10-20%, 10-15%, 15-50%, 15-40%, 15-30%, 15-25%, 15-20%, 20-50%, 20-40%, 20-30%, 20-25%, 25-50%, 25-40%, 25-30%, 30-50%, 30-40%, or 40-50%. In specific, but not limiting embodiments, the third layer is comprised of one or more stretchable polymers having a stretchability or elasticity of at least about 5%, 10%, 15%, 20%, 25%, 30%, 40%, or 50%.

In other embodiments, the third layer is relatively stiff as compared to at least one of the first or second layers.

In some embodiments, the third layer is occlusive or substantially occlusive. In other embodiments, the third layer is breathable.

In embodiments, the third layer has a thickness of about 0.5-40 mil. In non-limiting embodiments, the third layer has a thickness of between about 0.5-1 mil, 0.5-1.5 mil, 0.5-2 mil, 0.5-3 mil, 0.5-4 mil, 0.5-5 mil, 0.5-10 mil, 0.5-15 mil, 0.5-20 mil, 0.5-25 mil, 0.5-30 mil, 0.5-35 mil, 1-1.5 mil, 1-2 mil, 1-3 mil, 1-4 mil, 1-5 mil, 1-10 mil, 1-15 mil, 1-20 mil, 1-25 mil, 1-30 mil, 1-35 mil, 1-40 mil. 1.5-2 mil, 1.5-3 mil, 1.5-4 mil, 1.5-5 mil, 1.5-10 mil, 1.5-15 mil, 1.5-20 mil, 1.5-25 mil, 1.5-30 mil, 1.5-35 mil, 1.5-40 mil, 2-3 mil, 2-4 mil, 2-5 mil, 2-10 mil, 2-15 mil, 2-20 mil, 2-25 mil, 2-30 mil, 2-35 mil, 2-40 mil, 3-4 mil, 3-5 mil, 3-10 mil, 3-15 mil, 3-20 mil, 3-25 mil, 3-30 mil, 3-35 mil, 3-40 mil, 4-5 mil, 4-10 mil, 4-15 mil, 4-20 mil, 4-25 mil, 4-30 mil, 4-35 mil, 4-40 mil, 5-10 mil, 5-15 mil, 5-20 mil, 5-25 mil, 5-30 mil, 5-35 mil, 5-40 mil, 10-15 mil, 10-20 mil, 10-25 mil, 10-30 mil, 10-35 mil, 10-40 mil, 15-20 mil, 15-25 mil, 15-30 mil, 15-35 mil, 15-40 mil, 20-25 mil, 20-30 mil, 20-35 mil, 20-40 mil, 25-30 mil, 25-35 mil, 25-40 mil, 30-35 mil, 30-40 mil, or 35-40 mil. In specific, but not limiting embodiments, the third layer has a thickness of about 0.5 mil, 1 mil, 1.5 mil, 2 mil, 3 mil, 4 mil, 5 mil, 10 mil, 15 mil, 20 mil, 25 mil, 30 mil, 35 mil, or 40 mil.

In embodiments, the third layer is a non-woven or woven fabric formed of synthetic or natural fibers. In embodiments, the synthetic fibers are comprised of one or more polymer fibers. In embodiments, the third layer is a polymer film, polymer laminate, or polymer matrix. In embodiments, the polymer is selected from one or more of polyesters such as polyethylene terephthalate (PET), polyethylenes, vinyl acetates or copolymers thereof, polypropylenes, nylon, polystyrenes, polyvinylchloride, or polyurethanes, ethylene vinyl acetate (EVA) copolymers thereof, or mixtures/blends thereof. In embodiments, the third layer is a polymer film comprised of a polyethylene terephthalate/ethylene vinyl acetate laminate. In other embodiments, the third layer is comprised of polyethylene terephthalate. In embodiments, the natural fibers are comprised of at least one of cotton or silk. The third layer is attached or affixed to an adhesive/drug layer using any suitable means. In some embodiments, the third layer is affixed or attached to the adhesive/drug layer using a suitable adhesive.

Example 1 describes preparation of an exemplary transdermal delivery system comprising a composite backing layer. A stretchable or flexible polymer layer is laminated onto an occlusive backing using an adhesive. An adhesive formulation is prepared, coated onto a release liner and the formulation is laminated onto the polymer side of the composite backing laminate. Example 7 describes preparation of a further exemplary transdermal delivery system comprising a composite backing layer. A stretchable, woven fabric is laminated onto a polymer film using an adhesive. An adhesive drug formulation is prepared, coated onto a release liner and the formulation is laminated onto the polymer film side of the composite backing laminate.

Figure 5:
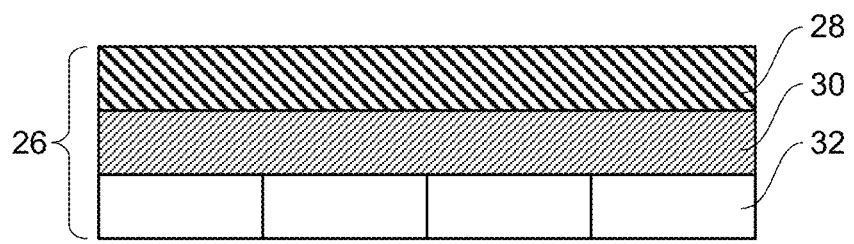
FIG. 5 is a side view illustrating an exemplary composite backing comprising separate pieces for a first or top layer.

In a second aspect, one or more layers of the composite backing is at least partially cut, incised or divided. In some embodiments, at least one layer comprises multiple cuts, incisions, or divisions through the layer such that at least one layer of the composite comprises several, separate pieces. FIG. 5 is a side view illustrating an exemplary composite backing comprising separate pieces for a first or top layer. In this aspect, the composite backing 26 comprises a first layer 28, a second adhesive layer 30, and a third layer 32 that may be occlusive or breathable. Any combination or all of the layers of the composite backing may be at least partially cut, incised or divided. In embodiments, at least one of the first layer or the third layer is at least partially cut, incised or divided. In embodiments, at least the third occlusive or breathable layer comprises separate pieces as shown in FIG. 5.

Figure 4A:
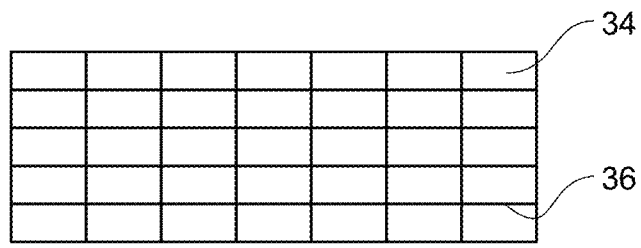
FIG. 4A is a top view illustration of a backing laminate layer.
Figure 4B:
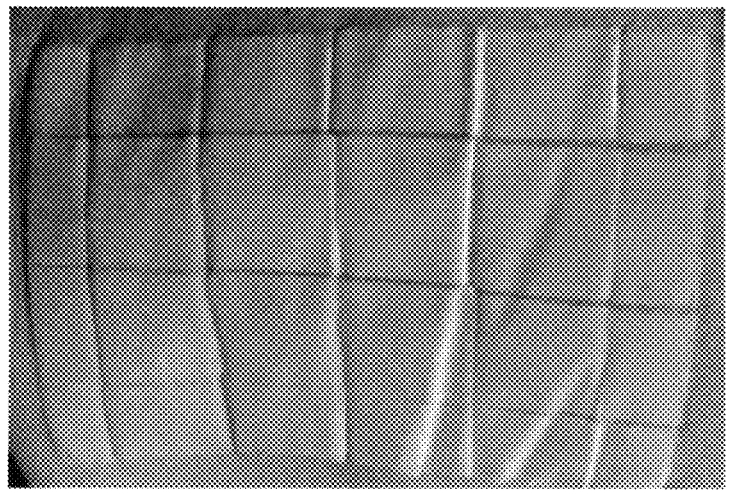
FIG. 4B is a top view image of a divided backing layer.

As seen FIG. 4A, one or more layers of the composite backing is at least partially cut, incised or divided. In some embodiments, at least the third layer 32 of the composite backing is at least partially cut, incised or divided. In the embodiment as shown in FIGS. 4A-4B, the third layer is at least partially cut, incised or divided such that the third layer is comprised of a plurality of portions or pieces. These cuts may be formed partially or completely through the layer. In an embodiment, the layer is kiss cut such that at least one layer is cut while at least one of the layers (e.g. an elastic, flexible or stretchable layer) remains at least partially intact. In embodiments, the elastic or flexible polymer layer holds the layer comprising the cuts or incisions. In some embodiments, both the elastic, flexible or stretchable layer and the adhesive layers are at least partially intact. FIG. 4A shows an exemplary grid pattern for the cuts or incisions 36. In some embodiments, the cut layer is comprised of individually separated pieces of material 34 formed by the cuts in the layer material. The separate pieces may be any appropriate shape or form. In embodiments, the separated pieces are rectangular or square. It will be appreciated that the cuts may be regular or irregular in shape. It will further be appreciated that the resulting pieces may be the same or different shapes. In some embodiments, one or more of the pieces are connected at one or more connection regions. FIG. 4B shows a layer formed of individual rectangular pieces of material. In some embodiments, the cut layer is formed of multiple pieces of a relatively stiff material as described above. Motion of the relatively stiff layer within the composite and/or against the skin will be dissipated at the cuts. The layer comprising the cuts/pieces will behave like multiple patches of smaller area applied. Where the cut layer is formed of separate pieces, the layer is conformable and/or stretchable along with the movement of skin. Further, the adhesion of each piece helps an adjacent piece because they are held or adhered together similar to a continuous layer.

In some embodiments, each piece of the cut layer has a surface area of between about 5-50 cm$^2$. In some embodiments, each piece of the cut layer has a surface area of between about 10-30 cm$^2$. In some embodiments, each piece has a surface area of about 10 cm$^2$, 15 cm$^2$, 20 cm$^2$, 25 cm$^2$, 30 cm$^2$, 35 cm$^2$, 40 cm$^2$, 45 cm$^2$, or 50 cm$^2$. In some embodiments, the pieces of the layer may comprise a similar size. In other embodiments, the pieces of the layer comprise different sizes.

Figure 9:
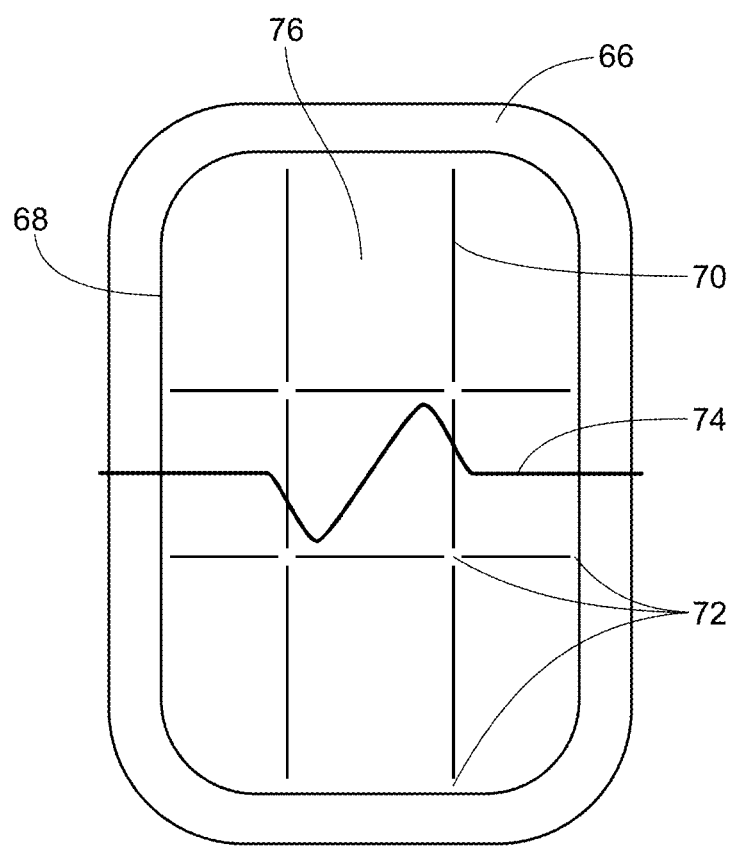
FIG. 9 is an illustration of a bottom-up view of a segmented patch layer in accord with embodiments described herein.

In some embodiments, the cuts, incisions or divisions extend at least partially along a planar surface of at least one layer of the composite backing. FIG. 9 is a top down view of a device as described herein in some embodiments. As seen in this embodiment, the cuts, incisions or divisions 70 extend along a portion of one or more layers 68 of the device, but do not extend across or along the entirety of the layer. In this embodiment, the cuts, incisions or divisions do not intersect. Instead, the layer(s) are intact at one or more of the edges and/or the areas where cross-wise cuts, incisions or divisions would intersect 72. Rather than being separate pieces, the partially cut portions of the layer 76 are at least partially connected. This embodiment further shows the overhang of the first layer 66.

Example 2 describes preparation of an exemplary layer comprising a discretely cut layer. A flexible polymer material is applied to a carrier formed of paper or other inert material. The carrier serves as a substrate to form the discretely cut layer. In embodiments, the flexible polymer is as described above including, but not limited to, a thin (0.5-1.0 mil) polyurethane film. An occlusive material is applied to the flexible polymer material using a suitable adhesive as known in the art. In some embodiments, the adhesive is selected from a polyisobutylene (PIB), an acrylate or acrylate co-polymer, or a silicone adhesive or binding agent. The resulting laminate comprises the carrier, flexible polymer, adhesive, and occlusive material. The laminate is at least partially cut such that the occlusive layer is separated into separated pieces. At least a portion of the flexible polymer layer remains intact.

Example 3 describes preparation of a transdermal delivery system using a composite backing layer comprising an occlusive layer kiss-cut into rectangular pieces.

The device includes at least one adhesive/drug layer 14 adjacent the composite backing layer 12. In embodiments, the adhesive layer is an adhesive matrix comprising the active agent as described above. The adhesive layer adheres to the backing layer and/or skin at the administration site. Preferably, the adhesive layer 14 is positioned adjacent the third or bottom layer 22 of the composite backing 12. The adhesive layer matrix serves to release the active agent to the skin as well as secure the patch to the skin.

In an embodiment, the adhesive/drug layer is an adhesive hydrogel-containing composition as described in U.S. Pat. No. 8,728,445, which is incorporated herein by reference. One suitable hydrogel-containing composition is comprised of a single, continuous hydrophilic phase. Another suitable composition comprises a discontinuous hydrophobic phase and a hydrophilic phase that is either continuous or discontinuous. In an embodiment, the hydrogel composition comprises a discontinuous hydrophobic phase comprising at least one hydrophobic polymer, a plasticizer such as an elastomer, a tackifying resin and/or other excipients; and a hydrophilic phase comprised of at least one crosslinked hydrophilic polymer.

The hydrophobic polymer may be a hydrophobic pressure-sensitive adhesive (PSA) polymer. In some embodiments, the hydrophobic polymer is a thermosetting polymer. In embodiments, the hydrophobic PSA polymers are cross-linked butyl rubbers, wherein a "butyl rubber," as well known in the art, is an isoprene-isobutylene copolymer typically having an isoprene content in the range of about 0.5 to 3 wt %, or a vulcanized or modified version thereof, e.g., a halogenated (brominated or chlorinated) butyl rubber. In some embodiments, the hydrophobic PSA polymer is butyl rubber crosslinked with polyisobutylene. Other suitable hydrophobic polymers include, for example, natural rubber adhesives, vinyl ether polymers, polysiloxanes, polyisoprene, butadiene acrylonitrile rubber, polychloroprene, atactic polypropylene, and ethylene-propylene-diene terpolymers (also known as "EPDM" or "EPDM rubber") (available as Trilene® 65 and Trilene® 67 from Uniroyal Chemical Co., Middlebury, Conn.). Still other suitable hydrophobic PSAs will be known to those of ordinary skill in the art and/or are described in the pertinent texts and literature. See, for example, the Handbook of Pressure-Sensitive Adhesive Technology, 2nd Ed., Satas, Ed. (New York: Von Nostrand Reinhold, 1989). In some particular embodiments, the hydrophobic polymers are the crosslinked butyl rubbers available in the Kalar® series from Elementis Specialties, Inc. (Hightstown, N.J.), including Kalar® 5200, Kalar® 5215, Kalar® 5246, and Kalar® 5275.

In some embodiments, the hydrophobic phase comprises a plasticizer. By "plasticizer" is meant that the component tends to decrease the glass transition temperature of the hydrophobic polymer and/or reduce its melt viscosity. Suitable plasticizing elastomers are natural and synthetic elastomeric polymers, including, for example, AB, ABA, and "multiarmed" (AB)x block copolymers, where for example, A is a polymerized segment or "block" comprising aryl-substituted vinyl monomers, preferably styrene, α-methyl styrene, vinyl toluene, and the like, B is an elastomeric, conjugated polybutadiene or polyisoprene block, and x has a value of 3 or more. In some embodiments, the plasticizer is an elastomer including butadiene-based and isoprene-based polymers, particularly styrene-butadiene-styrene (SBS), styrene-butadiene (SB), styrene-isoprene-styrene (SIS), and styrene-isoprene (SI) block copolymers, where "S" denotes a polymerized segment or "block" of styrene monomers, "B" denotes a polymerized segment or block of butadiene monomers, and "I" denotes a polymerized segment or block of isoprene monomers. Other suitable elastomers include radial block copolymers having a SEBS backbone (where "E" and "B" are, respectively, polymerized blocks of ethylene and butylene) and I and/or SI arms. Natural rubber (polyisoprene) and synthetic polyisoprene can also be used.

In some embodiments, the hydrophobic phase comprises a tackifying resin. The tackifying resin may be a relatively low molecular weight resin (weight average molecular weight generally less than about 50,000) having a fairly high glass transition temperature. Tackifying resins include, for example, rosin derivatives, terpene resins, and synthetic or naturally derived petroleum resins. In some embodiments, the tackifying resin is selected from the group of non-polar tackifying resins, such as Regalrez® 1085 (a hydrogenated hydrocarbon resin) and Regalite® Resins such as Regalite® 1900, available from Hercules, Escorez® 1304 (also a hydrocarbon resins) and Escorez® 1102 available from Exxon Chemical Company, Wingtack® 95 (a synthetic polyterpene resin), or Wingtack® 85, available from Goodyear Tire and Rubber.

In some embodiments, the hydrophobic phase comprises an optional antioxidant which serves to enhance the oxidative stability of the hydrogel composition. Other suitable plasticizers, tackifiers, and antioxidants are known in the art such as those described in U.S. Pat. No. 8,728,445, which is incorporated herein by reference.

In some embodiments, the composition comprises a discontinuous hydrophilic phase comprised of at least one crosslinked hydrophilic polymer that is insoluble in water under standard conditions of storage and use, but is water-swellable. In embodiments, the degree of crosslinking is selected so that the polymer will not melt during manufacture of the composition. Suitable hydrophilic polymers include, but are not limited to: crosslinked cellulosic polymers (such as crosslinked sodium carboxymethylcellulose); crosslinked acrylate polymers and copolymers; carbomers, i.e., hydroxylated vinylic polymers also referred to as "interpolymers," which are prepared by crosslinking a monoolefinic acrylic acid monomer with a polyalkyl ether of sucrose (commercially available under the trademark Carbopol® from the B. F. Goodrich Chemical Company); crosslinked acrylamide-sodium acrylate copolymers; gelatin; vegetable polysaccharides, such as alginates, pectins, carrageenans, or xanthan; starch and starch derivatives; and galactomannan and galactomannan derivatives. One particular crosslinked hydrophilic polymer is crosslinked sodium CMC, available as Aquasorb® A500 from Aqualon, a division of Hercules, Inc.

In some embodiments, the composition comprises a continuous hydrophilic phase. The continuous hydrophilic phase comprises a water-swellable, water-insoluble polymer, a blend of a hydro hydrophilic polymer and a complementary oligomer capable of hydrogen bonding thereto, and an optional low molecular weight plasticizer.

The water-swellable, water-insoluble polymer is generally capable of at least some degree of swelling when immersed in an aqueous liquid but is insoluble in water within a selected pH range, generally up to a pH of at least about 7.5 to 8.5. The polymer may be comprised of a cellulose ester, for example, cellulose acetate, cellulose acetate propionate (CAP), cellulose acetate butyrate (CAB), cellulose propionate (CP), cellulose butyrate (CB), cellulose propionate butyrate (CPB), cellulose diacetate (CDA), cellulose triacetate (CTA), or the like. These cellulose esters are described in U.S. Pat. Nos. 1,698,049, 1,683,347, 1,880,808, 1,880,560, 1,984,147, 2,129,052, and 3,617,201, and may be prepared using techniques known in the art or obtained commercially. Commercially available cellulose esters suitable herein include CA 320, CA 398, CAB 381, CAB 551, CAB 553, CAP 482, CAP 504, all available from Eastman Chemical Company, Kingsport, Tenn. Such cellulose esters typically have a number average molecular weight of between about 10,000 and about 75,000. Other suitable water-swellable polymers are known in the art as described, for example, in U.S. Pat. No. 8,728,445, incorporated by reference herein.

The hydrogel composition may also include conventional additives such as fillers, preservatives, pH regulators, softeners, thickeners, pigments, dyes, refractive particles, stabilizers, toughening agents, detackifiers, pharmaceutical agents, and permeation enhancers. In those embodiments wherein adhesion is to be reduced or eliminated, conventional detackifying agents may also be used. These additives, and amounts thereof, are selected in such a way that they do not significantly interfere with the desired chemical and physical properties of the hydrogel composition.

Absorbent fillers may be advantageously incorporated to control the degree of hydration when the adhesive is on the skin or other body surface. Such fillers can include microcrystalline cellulose, talc, lactose, kaolin, mannitol, colloidal silica, alumina, zinc oxide, titanium oxide, magnesium silicate, magnesium aluminum silicate, hydrophobic starch, calcium sulfate, calcium stearate, calcium phosphate, calcium phosphate dihydrate, woven and non-woven paper and cotton materials. Other suitable fillers are inert, i.e., substantially non-adsorbent, and include, for example, polyethylenes, polypropylenes, polyurethane polyether amide copolymers, polyesters and polyester copolymers, nylon and rayon. A preferred filler is colloidal silica, e.g., Cab-O-Sil® (Cabot Corporation, Boston Mass.).

Preservatives include, by way of example, p-chloro-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, and propylene glycol.

Compounds useful as pH regulators include, but are not limited to, glycerol buffers, citrate buffers, borate buffers, phosphate buffers, or citric acid-phosphate buffers may also be included so as to ensure that the pH of the hydrogel composition is compatible with that of an individual's body surface.

Suitable softeners include citric acid esters, such as triethylcitrate or acetyl triethylcitrate, tartaric acid esters such as dibutyltartrate, glycerol esters such as glycerol diacetate and glycerol triacetate; phthalic acid esters, such as dibutyl phthalate and diethyl phthalate; and/or hydrophilic surfactants, preferably hydrophilic non-ionic surfactants, such as, for example, partial fatty acid esters of sugars, polyethylene glycol fatty acid esters, polyethylene glycol fatty alcohol ethers, and polyethylene glycol sorbitan-fatty acid esters.

Preferred thickeners herein are naturally occurring compounds or derivatives thereof, and include, by way of example: collagen; galactomannans; starches; starch derivatives and hydrolysates; cellulose derivatives such as methyl cellulose, hydroxypropylcellulose, hydroxyethyl cellulose, and hydroxypropyl methyl cellulose; colloidal silicic acids; and sugars such as lactose, saccharose, fructose and glucose. Synthetic thickeners such as polyvinyl alcohol, vinylpyrrolidone-vinylacetate-copolymers, polyethylene glycols, and polypropylene glycols may also be used.

In embodiments, the adhesive drug layer is a composition that phase separates when moist as described in U.S. Pat. No. 8,481,059, which is incorporated herein by reference.

The adhesive/drug layer comprises one or more drugs, active agents, and/or therapeutic agents. One or more active agents can be included in the composition of the invention. Suitable active agents that may be incorporated into the adhesives of the invention, include the broad classes of compounds normally delivered through body surfaces and membranes such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; anti-inflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof.

In some embodiments, the adhesive/drug layer comprises one or more drugs, active agents, and/or therapeutic agents for the treatment of Alzheimer's disease, dementia, and schizophrenia. In some embodiments, adhesive/drug layer comprises one or more drugs including, but not limited to donepezil and/or memantine.

The adhesive/drug layer may further comprise one or more permeation enhancers. With some active agents, it may be desirable to administer the agent along with a suitable permeation enhancer in order to achieve a therapeutically effective flux through the skin or mucosa. Selection of suitable permeation enhancers will depend upon the agent being delivered, as well as the enhancer's compatibility with the other components of the adhesive. Exemplary permeation enhancers include, by way of illustration and not limitation, sulfoxides such as dimethylsulfoxide and decylmethylsulfoxide; ethers such as diethylene glycol monoethyl ether and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin; the 1-substituted azacycloheptan-2-ones, particularly 1-n-dodecylcyclazacycloheptan-2-one; alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate; amides and other nitrogenous compounds such as urea, dimethylacetamide, dimethylformamide, 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid; and mixtures thereof.

The release of active agents "loaded" into the adhesive of the invention typically involves both absorption of water and desorption of the agent via a swelling-controlled diffusion mechanism. Active agent-containing adhesives may be included in adhesive cushions, wound dressings, transdermal drug delivery devices and the like.

In embodiments, the transdermal delivery system includes an optional release liner 16 that at least partially contacts the adhesive layer. The release liner is a removable covering that prevents loss of the active agent from the adhesive layer during storage and/or protects the device against contamination. The release liner is typically a disposable layer that is removed prior to application of the device to the treatment site. In some embodiments, the release liner preferably does not absorb components of the adhesive layer, including the active agent. In some embodiments, the release liner preferably impermeable to components of the adhesive layer (including the active agent) and prevents release of components of the adhesive layer through the release liner. By impermeable, it is meant that the release liner prevents all or substantially all of the components of the adhesive layer from passing completely through the release liner. In some embodiments, the release liner is easily removed or stripped from the adhesive/drug layer without removing a portion or a substantial portion of the adhesive drug layer. In some embodiments, the release liner is formed of one or more of a film, non-woven fabric, woven fabric, laminate, and combinations thereof. In some embodiments, the release liner is a silicone-coated polymer film or paper. In some non-limiting embodiments, the release liner is a silicone-coated polyethylene terephthalate (PET) film, a polyester film, a silicone-coated polyester film, a fluorocarbon film, or a fluorocarbon or fluorosilicone coated polymer film. In some embodiments, the material for the release liner is treated with one or more of silicone, fluorocarbons, or fluorosilicones. In one embodiment, the release liner is a comprised of a fluorocarbon or fluorosilicone coated PET film. In other embodiments, the release liner is comprised of a polyester foil or other metalized laminate. In some embodiments, the release liner may include features to increase ease of removal. In some embodiment, the release liner includes a slit or cut 74 as shown in FIG. 9 to assist in removal of the liner from the device.

The activity of a transdermal delivery system is defined (and dependent upon) the release rate of the active agent from the system, the total duration of release from the system, and the surface area of the delivery system.

In some embodiments, the backing layer overlays or overhangs at least one edge of at least one of the segmented patch layers. In some embodiments, the backing layer overhangs about 0.5-1.0 cm of at least one edge of at least one of the segmented patch layers.

Figure 6A:
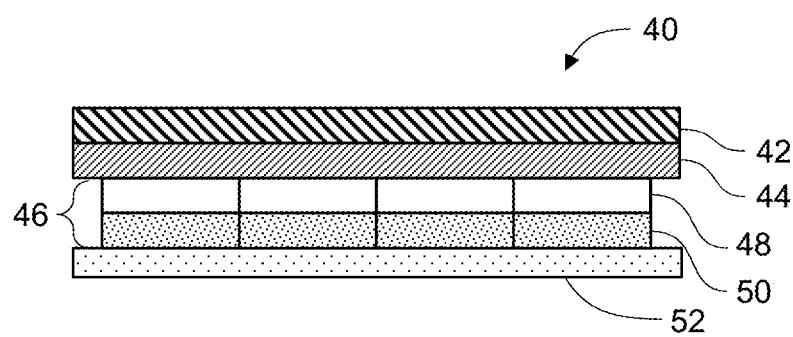
FIGS. 6A-6C are illustrations of transdermal patches having a segmented patch layer in accord with embodiments described herein.
Figure 6B:
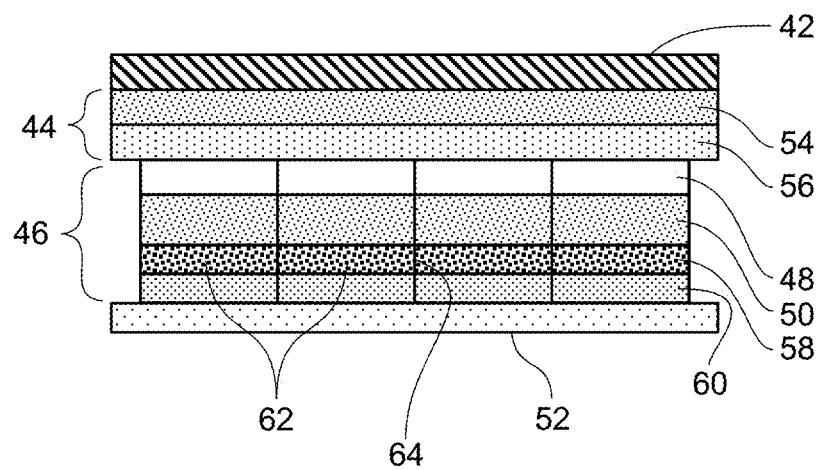
Figure 6C:
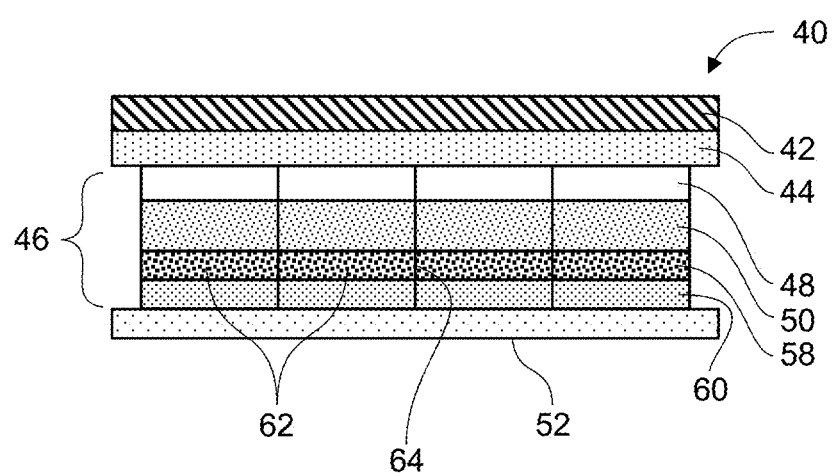

FIGS. 6A-6C show some embodiments of an exemplary transdermal patch, device or system, generally designated at 40, having internal segmented layers therein. In this embodiment, the device includes a backing layer 42, one or more optional adhesive interfacing layers 44, a segmented intermediate layer 46, and an optional release liner 52. In embodiments, the intermediate layer comprises an adhesive layer 50 comprising the drug or therapeutic agent. In embodiments, the intermediate layer comprises the adhesive drug layer 50 and a backing layer 48. In some embodiments, one or more of the backing layer, interfacing layer(s), and intermediate layer(s) are laminated together to form the transdermal patch. In some embodiments, one or more of the backing layer, interfacing layer(s), and intermediate layer(s) are at least partially segmented. In the embodiment as shown in FIG. 6C, the transdermal delivery system 40 comprises a backing or overlay layer 42, an adhesive interfacing layer 44, a segmented intermediate layer 46, and a release liner 52. In this embodiment, the segmented intermediate layer comprises a backing layer 48 that may be occlusive or breathable, an adhesive drug layer 50, a rate-controlling tie layer or membrane 58, and a contact adhesive layer 60.

Figure 8:
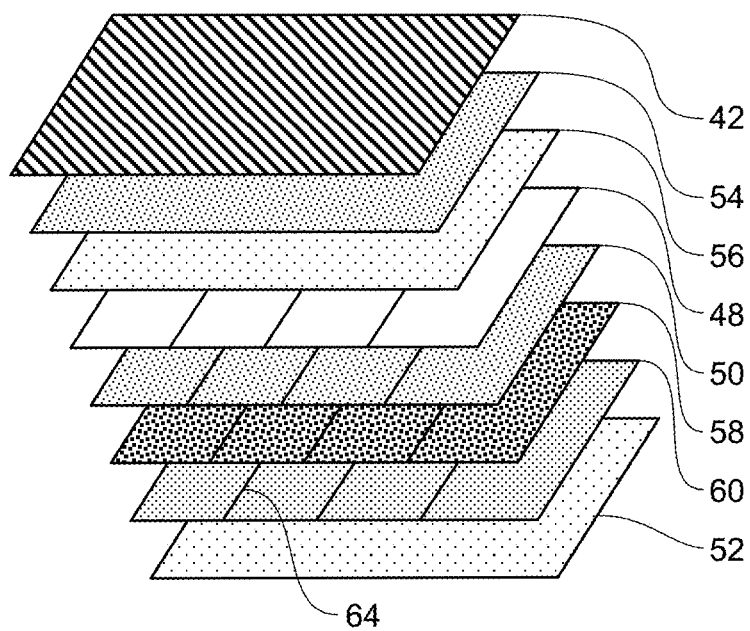
FIG. 8 is an illustration of an exploded view of a transdermal patch in accord with embodiments described herein.

The interfacing adhesive layer or layers adheres or connects the backing layer to the segmented patch layers (at least the uppermost layer). In embodiments, the interfacing layer is comprised of one or more polymers selected from acrylates, polyisobutylenes, silicone adhesives, polystyrene butyl rubber, polyethylene vinyl acetate and copolymers thereof. In some embodiments, the interfacing adhesive layers are comprised of a cross-linked acrylate adhesive or its mixture. Exemplary cross-linked acrylate adhesives include the adhesives sold under the name Duro-Tak®. Specific, but not limiting, Duro-Tak® adhesives include Duro-Tak® 387-2516, Duro-Tak® 387-2852, Duro-Tak® 87-2052 or mixtures thereof. In some embodiments, at least one interfacing adhesive layer comprises a polyisobutylene (PIB) or acrylate adhesive containing crospovidone or colloidal silicone dioxide matrix modifiers. As shown in FIG. 6B, in some embodiments the interfacing layer comprises one or more adhesive layers. In some embodiments, the interfacing layer comprises a plurality of adhesive layers. In some embodiments as shown in FIGS. 6B and 8, the interfacing layer comprises at least a first adhesive layer 54 and a second adhesive layer 56. In these embodiments, the first adhesive layer is formed of a material having good adhesion to the backing layer material. In embodiments, the first adhesive layer should not bleed into the backing layer, especially where the backing layer is a fabric. The second adhesive layer is preferably formed of a material having good adhesion to the proximal layer of the segmented patch. In some embodiments, the second adhesive layer is formed of a material having good adhesion to skin. It will be appreciated that the interfacing layer is comprised of at least one or a plurality of adhesive layers.

In some embodiments, the interfacing adhesive layer or at least one layer of the interfacing layer overlays or overhangs at least one edge of at least one of the segmented patch layers. In some embodiments, the adhesive layer or layers overhang about 0.5-1.0 cm of at least one edge of at least one of the segmented patch layers. It will be appreciated that one or more or all of the backing layer, first adhesive layer and second adhesive layer may overlay or overhang at least one edge of the segmented patch layers. It will further be appreciated that the backing layer, first adhesive layer and/or the second adhesive layer may overlay or overhang the same or different amounts.

In some embodiments, one or more of the interfacing adhesive layers is comprised of one or more pressure sensitive adhesive polymers. In embodiments, the adhesive polymer is an acrylic polymer. In some embodiments, the adhesive polymer is an acrylic pressure sensitive adhesive polymer. In embodiments, the acrylic polymer is an acrylate or acrylate copolymer, or polyacrylate adhesive polymer. An acrylic pressure sensitive adhesive polymer is a polyacrylate that is a polymer of copolymer of a monomer or monomers selected from acrylic acid esters and methacrylic acid esters. Other monomers, such as acrylic acid and vinyl acetate, may be present. In embodiments, the acrylic polymer is based on acrylic esters such as 2-ethylhexyl acrylate (2-EHA) and ethyl acrylate. In some embodiments, the polyacrylate polymer is a polymer or a copolymer of a monomer or monomers selected from acrylic acid and vinyl acetate. In embodiments, the acrylic polymer adhesive has pendent carboxyl (—COOH) or hydroxyl (—OH) functional groups. In embodiments, the acrylic polymer adhesive comprises at least one of polyacrylate, polymethacrylate, derivatives thereof, and co-polymers thereof. In embodiments, the acrylic adhesive is comprised of an acrylate copolymer comprising acrylic ester monomers or vinyl acetate monomers. Exemplary acrylate copolymers are sold under the trade-name DURO-TAK®.

In some embodiments, one or more of the interfacing adhesive layers is comprised of one or more polymers comprising a pyrrolidone group, polyisobutylenes, polybutenes, mixtures and co-polymers thereof. In some embodiments, one or more of the interfacing adhesive layers is comprised of a crosslinked polyvinylpyrrolidone. One exemplary polyvinylpyrrolidone is a crospovidone such as the micronized crospovidone sold under the name Kollidon® CL-M available from BASF. In embodiments, the adhesive matrix comprises a blend or mixture of polyisobutylene and polybutene polymers. Polyisobutylene is a vinyl polymer comprised of the isobutylene monomer. Polybutene is a viscous, non-drying, liquid polymer, prepared by copolymerization of 1- and 2-butene with a small quantity of isobutylene. In some embodiments, the polybutene in one embodiment has a molecular weight of between about 750-6000 Daltons, preferably between about 900-4000 Daltons, and preferably between about 900-3000 Daltons. In some embodiments the mixture comprises polybutene in the polyisobutylene blend at about 40 weight percent. More generally, the polybutene is present in the polyisobutylene blend in an amount between 20-50 weight percent, or between 25-45 weight percent.

In some embodiments, one or more of the interfacing adhesive layers is comprised of one or more silicone based adhesives, a medical adhesive, a tissue adhesive, a surgical adhesive, or a combination of adhesives. It will be appreciated that the adhesives and features as described for above embodiments may be used in the present embodiments.

In embodiments, the interfacing adhesive layers have a thickness of about 0.5-5 mil. In non-limiting embodiments, the interfacing adhesive layers have a thickness of between about 0.5-0.75 mil, 0.5-1 mil, 0.5-1.5 mil, 0.5-2 mil, 0.5-2.5 mil, 0.5-3 mil, 0.5-3.5 mil, 0.5-4 mil, 0.5-4.5 mil, 0.75-1 mil, 0.75-1.5 mil, 0.75-2 mil, 0.75-2.5 mil, 0.75-3 mil, 0.75-3.5 mil, 0.75-4 mil, 0.75-4.5 mil, 0.75-5 mil, 1-1.5 mil, 1-2 mil, 1-2.5 mil, 1-3 mil, 1-3.5 mil, 1-4 mil, 1-4.5 mil, 1-5 mil, 1.5-2 mil, 1.5-2.5 mil, 1.5-3 mil, 1.5-3.5 mil, 1.5-4 mil, 1.5-4.5 mil, 1.5-5 mil, 2-2.5 mil, 2-3 mil, 2-3.5 mil, 2-4 mil, 2-4.5 mil, 2-5 mil, 2.5-3 mil, 2.5-3.5 mil, 2.5-4 mil, 2.5-4.5 mil, 2.5-5 mil, 3-3.5 mil, 3-4 mil, 3-4.5 mil, 3-5 mil, 3.5-4 mil, 3.5-4.5 mil, 3.5-5 mil, 4-4.5 mil, 4-5 mil, or 4.5-5 mil. In some specific but non-limiting embodiments, the interfacing adhesive layers have a thickness of about 0.5 mil, 1 mil, 1.5 mil, 2 mil, 2.5 mil, 3 mil, 3.5 mil, 4 mil, 4.5 mil, or 5 mil.

Figure 7:
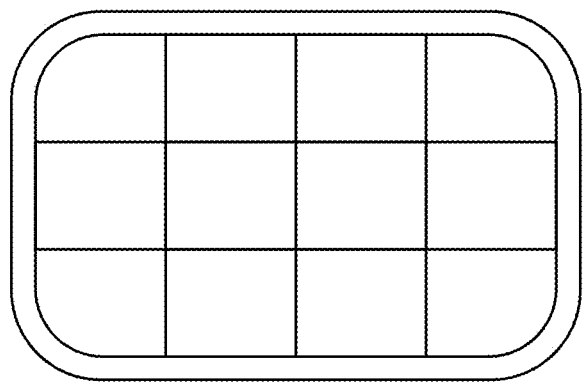
FIG. 7 is an illustration of a top-down view of the segmented patch layer in accord with embodiments described herein.

An intermediate layer 46 is positioned between the interfacing adhesive layer 44 and the optional release liner 52 or skin. In some embodiments, at least the intermediate layer is at least partially segmented, divided, or cut. In some embodiments, the intermediate layer is segmented, divided, cut, or otherwise separated into a plurality of sectioned parts. FIG. 7 is an illustration of the segmented intermediate layer 46 as viewed from above. The overhang of the backing layer 42 and/or interfacing adhesive layer 44 is shown around the circumference of the intermediate layer. In this embodiment, the segments are made by cuts or divisions 64 in a crosshatch pattern. In other words, the segments are made by cuts or divisions along the length and width (in this top-down view) of the intermediate layer. It will be appreciated that the segments may be formed by cuts or divisions along the length or width of the intermediate layer. In this embodiment, the patch segments or portions 62 will have an elongated strip shape. The cuts or divisions preferably are made through the entirety of the intermediate layer. Thus, the intermediate layer is made up of a plurality of patch segments or portions 62. The cuts or divisions allow movement of the portions within the patch including movement in different directions.

As noted above, in some embodiments, the cuts or incisions do not extend across the entirety of the layer such that the layer is not divided into separate segments. As shown in FIG. 9, the cuts or incisions may not intersect and/or may not extend to an edge of the layer.

Each segment or portion may have size (from a top/bottom view) of about 2-30 cm². In some embodiments, each segment or portion may have a size of about 2-25 cm², 2-20 cm², 2-15 cm², 2-10 cm², 2-5 cm², 5-30 cm², 5-25 cm², 5-20 cm², 5-15 cm², 5-10 cm², 10-30 cm², 10-25 cm², 10-20 cm², 10-15 cm², 15-30 cm², 15-25 cm², 15-20 cm², 20-30 cm², 20-25 cm², or about 25-30 cm². It will be appreciated that the segments may have the same or different sizes. For example, the size of the segments near the outer edge of the patch may have a larger or smaller size than segments positioned near the center of the patch. The segments may have any shape as suitable for forming the intermediate layer and providing movement within the patch. In some embodiments, the segments have a square, rectangular or other polygonal shape. It will be appreciated that the segments may all have the same or different shapes within a single layer.

In embodiments, the intermediate layer comprises at least one or a plurality of layers. In embodiments, the intermediate layer comprises at least an intermediate backing layer 48 and an adhesive drug layer 50 comprising an active agent, therapeutic agent or drug. As seen in FIG. 6A, the adhesive backing layer 48 is positioned between the interfacing layer 44 or layers and the adhesive drug layer 50. It will be appreciated that one or more of the plurality of individual layers of the intermediate layer may include cuts, incisions or divisions at least partially through the respective layer.

The intermediate backing layer may be formed of materials as described for backing layers above. In some embodiments, the intermediate backing layer is formed of an occlusive material. In some embodiments, the intermediate backing layer is formed of an occlusive polymer film or laminate. In other embodiments, the intermediate backing layer is formed of a breathable material. In some non-limiting embodiments, the intermediate backing layer comprises a polymer film comprised of a polymer selected from at least one of polyesters, polyethylenes, polypropylenes, nylon, and/or polystyrenes. In some embodiments, the polymer is selected from at least one of polyethylene terephthalate, ethylene vinyl acetate, polyethylene vinylacetate copolymer, polystyrene, and/or polyvinylchloride, and copolymers thereof. In one embodiment the intermediate backing layer is comprised of a polyethylene terephthalate/ethylene vinyl acetate laminate such as the Scotchpak™ 1012 (3M).

The intermediate layer further comprises one or more adhesive drug (active agent or therapeutic agent) layers 50 positioned between the intermediate backing layer and the release liner 52 where present. In embodiments, the adhesive drug layer comprises one or more active agent, therapeutic agent or drug as described above. The adhesive/drug layer as described above is useful for use in this embodiment.

In some embodiments, the intermediate layer comprises one or more additional layers. In some embodiments, the intermediate layer includes at least one tie layer 58. In some embodiments, the tie layer is positioned between the adhesive drug layer and the release liner where present. In some embodiments, the tie layer is an adhesive tie layer as described above. In some embodiments, the tie layer is comprised of a nonwoven fabric or a nonwoven, porous polymer membrane material. In some embodiments, the tie layer is a rate controlling membrane. In one non-limiting embodiment, the tie layer is comprised of a microporous polypropylene film. One exemplary film is the Celgard 2400 microporous film.

In some embodiments, the intermediate layer comprises one or more contact adhesive layers 60 positioned between the adhesive drug layer or tie layer, where present, and the release liner, where present. The contact adhesive layer adheres the patch to the subject's skin. Thus, the contact adhesive layer may be formed of one or more adhesives useful for adhering a patch to skin as described above.

FIG. 8 is an exploded view of one embodiment of a transdermal patch 40 comprising a segmented intermediate layer 46. The patch in this embodiment comprises, in order, a bi-elastic fabric backing layer 42, a first interfacing adhesive layer 54 formed of a first polymer film, a second interfacing adhesive layer 56, formed of a second polymer film that is different than the first polymer film, a segmented intermediate layer 46, and a protective release liner 52. The segmented intermediate layer comprises an occlusive backing layer 48, an adhesive drug layer 50, a rate-controlling tie layer 58, and a contact adhesive layer 60.

In embodiments, the backing layer has a thickness of between about 0.5-3 mil. In some embodiments, the backing layer has a thickness of about 0.5-0.75 mil, 0.5-1 mil, 0.5-1.5 mil, 0.5-2 mil, 0.5-2.5 mil, 0.75-1 mil, 0.75-1.5 mil, 0.75-2 mil, 0.75-2.5 mil, 0.75-3 mil, 1-1.5 mil, 1-2 mil, 1-2.5 mil, 1-3 mil, 1.5-2 mil, 1.5-2.5 mil, 1.5-3 mil, 2-2.5 mil, 2-3 mil, or 2.5-3 mil. In embodiments, the adhesive drug layer has a thickness of between about 1 to 25 mil. In some embodiments, the adhesive drug layer has a thickness of between about 1-20 mil, 1-15 mil, 1-10 mil, 1-5 mil, 5-25 mil, 5-20 mil, 5-15 mil, 5-10 mil, 10-25 mil, 10-20 mil, 10-15 mil, 15-25 mil, 15-20 mil, or 15-20 mil. In some embodiments, the rate-controlling tie layer has a thickness of between about 0.5 to 10 mil. In some embodiments, the tie layer has at thickness of about 0.5-9 mil, 0.5-8 mil, 0.5-7 mil, 0.5-6 mil, 0.5-5 mil, 0.5-4 mil, 0.5-3 mil, 0.5-2 mil, 0.5-1.5 mil, 0.5-1 mil, 0.5-0.75 mil, 0.75-10 mil, 0.75-9 mil, 0.75-8 mil, 0.75-7 mil, 0.75-6 mil, 0.75-5 mil, 0.75-4 mil, 0.75-3 mil, 0.75-2 mil, 0.75-1.5 mil, 0.75-1 mil, 1-10 mil, 1-9 mil, 1-8 mil, 1-7 mil, 1-6 mil, 1-5 mil, 1-4 mil, 1-3 mil, 1-2 mil, 1-1.5 mil, 1.5-10 mil, 1.5-9 mil, 1.5-8 mil, 1.5-7 mil, 1.5-6 mil, 1.5-5 mil, 1.5-4 mil, 1.5-3 mil, 1.5-2 mil, 2-10 mil, 2-9 mil, 2-8 mil, 2-7 mil, 2-6 mil, 2-5 mil, 2-4 mil, 2-3 mil, 3-10 mil, 3-9 mil, 3-8 mil, 3-7 mil, 3-6 mil, 3-5 mil, 3-4 mil, 4-10 mil, 4-9 mil, 4-8 mil, 4-7 mil, 4-6 mil, 4-5 mil, 5-10 mil, 5-9 mil, 5-8 mil, 5-7 mil, 5-6 mil, 6-10 mil, 6-9 mil, 6-8 mil, 6-7 mil, 7-10 mil, 7-9 mil, 7-8 mil, 8-10 mil, 8-9 mil, or 9-10 mil. In some embodiments, the contact adhesive layer has a thickness of about 1 to 5 mil. In some embodiments, the contact adhesive layer has a thickness of about 1-4 mil, 1-3 mil, 1-2 mil, 2-5 mil, 2-4 mil, 2-3 mil, 3-5 mil, 3-4 mil, or 4-5 mil.

Examples 4-6 describe in vivo adhesion studies of patches including a segmented layer and having various formulations and configurations. The results of these studies are presented in Table 1.

TABLE 1

Adhesion Study Results

| Formulation | Example 4 | | | Example 5 | | | Example 6 | |
|---|---|---|---|---|---|---|---|---|
| # Test subjects | 18 (total) | 9 | 9 | 14 (total) | 7 | 7 | 7 | |
| Breathable Top Layer | Control | KOB | PU | KOB | KOB | KOB | KOB | KOB |
| Border distance (cm) | 0 | 0 | 0 | 0 | 0.5 | 1 | 0 | 0.5 |
| Mean Adhesion Score | 2.2 | 1.3 | 1.8 | 1.9 | 1.8 | 0.2 | 1.0 | 0.5 |

Example 4 considered the effect of a segmented intermediate layer on a transdermal patch as well as the effect of the backing layer composition on patch adhesion. Both of the patches including a segmented intermediate layer had a lower adhesion score indicating a greater percentage of the patch area adhered to the skin over the seven days of wear. For both of the segmented patches, the adhesion score was <2 so that ≥75% to <90% of the patch remained adhered to the skin over the test period. In contrast, the patch without a segmented layer had a much lower adhesion score where at least 25% (and up to half) of the patch lifted off the skin. Among the segmented patches, the patch comprising a woven bi-elastic polyester fabric (KOB 053 available from Karl Otto GmbH & Co.) as the backing layer had better adhesion than the patches having a polyurethane film backing layer.

Example 5 considered the effect of having the backing layer overhang the segmented intermediate layer. Transdermal patches were prepared with the same composition and layers. A control patch had no overhang where the edge of the backing layer was flush with the edge of the intermediate layer. The control was compared to patches having an overhang of 0.5 cm or 1.0 cm. As seen in Table 1, the patch having the 1.0 cm had exceptional adhesion where nearly 90% of the patch area remained adhered to the skin. The control and 0.5 cm overhang patches both had good adhesion with an adhesion score of less than 2 so that ≥75% to <90% of the patch remained adhered. The use of a border or overhang improved adhesion as compared to the patch without a border.

Example 6 considered the effect of different compositions and configurations of the segmented intermediate layer on adhesion. A control patch without overhang (where the edge of the backing layers was flush with the edge of the intermediate layer) was compared to a patch having an overhang of a 0.5 cm border. As seen in Table 1, the patch having a 0.5 cm border had over 90% adhesion. Thus, an improvement in adhesion over the patch with an overhang may be achieved by adjusting the formulation.

Thus, segmenting at least a portion of the transdermal patch provided an increase in skin adhesion, especially over an extended wear duration.

The transdermal patch including a segmented portion may be prepared to have a thickness such that the desired amount of drug formulation is contained within the patch including the desired components while maintaining a thickness that is wearable and comfortable for the subject as described above.

In some embodiments, the transdermal patch has a size or surface area of about 5-200 cm$^2$. In some non-limiting embodiments, the transdermal patch has a size or surface area of about 5-10 cm$^2$, 5-15 cm$^2$, 5-20 cm$^2$, 5-25 cm$^2$, 5-30 cm$^2$, 5-40 cm$^2$, 5-45 cm$^2$, 5-50 cm$^2$, 5-60 cm$^2$, 5-70 cm$^2$, 5-75 cm$^2$, 5-80 cm$^2$, 5-90 cm$^2$, 5-100 cm$^2$, 5-125 cm$^2$, 5-150 cm$^2$, 5-175 cm$^2$, 10-15 cm$^2$, 10-20 cm$^2$, 10-25 cm$^2$, 10-30 cm$^2$, 10-40 cm$^2$, 10-45 cm$^2$, 10-50 cm$^2$, 10-60 cm$^2$, 10-70 cm$^2$, 10-75 cm$^2$, 10-80 cm$^2$, 10-90 cm$^2$, 10-100 cm$^2$, 10-125 cm$^2$, 10-150 cm$^2$, 10-175 cm$^2$, 10-200 cm$^2$, 15-20 cm$^2$, 15-25 cm$^2$, 15-30 cm$^2$, 15-40 cm$^2$, 15-45 cm$^2$, 15-50 cm$^2$, 15-60 cm$^2$, 15-70 cm$^2$, 15-75 cm$^2$, 15-80 cm$^2$, 15-90 cm$^2$, 15-100 cm$^2$, 15-125 cm$^2$, 15-150 cm$^2$, 15-175 cm$^2$, 15-200 cm$^2$, 20-25 cm$^2$, 20-30 cm$^2$, 20-40 cm$^2$, 20-45 cm$^2$, 20-50 cm$^2$, 20-60 cm$^2$, 20-70 cm$^2$, 20-75 cm$^2$, 20-80 cm$^2$, 20-90 cm$^2$, 20-100 cm$^2$, 20-125 cm$^2$, 20-150 cm$^2$, 20-175 cm$^2$, 20-200 cm$^2$, 25-30 cm$^2$, 25-40 cm$^2$, 25-45 cm$^2$, 25-50 cm$^2$, 25-60 cm$^2$, 25-70 cm$^2$, 25-75 cm$^2$, 25-80 cm$^2$, 25-90 cm$^2$, 25-100 cm$^2$, 25-125 cm$^2$, 25-150 cm$^2$, 25-175 cm$^2$, 25-200 cm$^2$, 30-40 cm$^2$, 30-45 cm$^2$, 30-50 cm$^2$, 30-60 cm$^2$, 30-70 cm$^2$, 30-75 cm$^2$, 30-80 cm$^2$, 30-90 cm$^2$, 30-100 cm$^2$, 30-125 cm$^2$, 30-150 cm$^2$, 30-175 cm$^2$, 30-200 cm$^2$, 40-45 cm$^2$, 40-50 cm$^2$, 40-60 cm$^2$, 40-70 cm$^2$, 40-75 cm$^2$, 40-80 cm$^2$, 40-90 cm$^2$, 40-100 cm$^2$, 40-125 cm$^2$, 40-150 cm$^2$, 40-175 cm$^2$, 40-200 cm$^2$, 45-50 cm$^2$, 45-60 cm$^2$, 45-70 cm$^2$, 45-75 cm$^2$, 45-80 cm$^2$, 45-90 cm$^2$, 45-100 cm$^2$, 45-125 cm$^2$, 45-150 cm$^2$, 45-175 cm$^2$, 45-200 cm$^2$, 50-60 cm$^2$, 50-70 cm$^2$, 50-75 cm$^2$, 50-80 cm$^2$, 50-90 cm$^2$, 50-100 cm$^2$, 50-125 cm$^2$, 50-150 cm$^2$, 50-175 cm$^2$, 50-200 cm$^2$, 60-70 cm$^2$, 60-75 cm$^2$, 60-80 cm$^2$, 60-90 cm$^2$, 60-100 cm$^2$, 60-125 cm$^2$, 60-150 cm$^2$, 60-175 cm$^2$, 60-200 cm$^2$, 70-75 cm$^2$, 70-80 cm$^2$, 70-90 cm$^2$, 70-100 cm$^2$, 70-125 cm$^2$, 70-150 cm$^2$, 70-175 cm$^2$, 70-200 cm$^2$, 80-90 cm$^2$, 80-100 cm$^2$, 80-125 cm$^2$, 80-150 cm$^2$, 80-175 cm$^2$, 80-200 cm$^2$, 90-100 cm$^2$, 90-125 cm$^2$, 90-150 cm$^2$, 90-175 cm$^2$, 90-200 cm$^2$, 100-125 cm$^2$, 100-150 cm$^2$, 100-175 cm$^2$, 100-200 cm$^2$, 125-150 cm$^2$, 125-175 cm$^2$, 125-200 cm$^2$, 150-175 cm$^2$, 150-200 cm$^2$, or 175-200 cm$^2$. In specific, but not limiting, embodiments, the transdermal patch has a size or surface area of about 5 cm$^2$, 10 cm$^2$, 15 cm$^2$, 20 cm$^2$, 25 cm$^2$, 30 cm$^2$, 40 cm$^2$, 45 cm$^2$, 50 cm$^2$, 60 cm$^2$, 70 cm$^2$, 75 cm$^2$, 80 cm$^2$, 90 cm$^2$, 100 cm$^2$, 125 cm$^2$, 150 cm$^2$, 175 cm$^2$, or 200 cm$^2$.

III. Methods of Treatment

Based on the exemplary compositions and devices described herein, and the data showing release effective long term administration of the device, a method for prolonged or long term administration of an active agent is provided herein.

The methods and systems described herein may be used for treating or preventing any condition receptive to treatment with a therapeutic agent, drug or active agent as described herein. The methods and systems described herein are particularly useful for long term transdermal administration of the therapeutic agent, drug or active agent. In embodiments, the transdermal device is suitable for administration of the active agent or agents for at least about 3-14 days or more.

IV. Examples

The following examples are illustrative in nature and are in no way intended to be limiting.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, patent publications, and other publications mentioned herein are hereby incorporated by reference in their entirety. Where a patent, application, or publication contains express definitions, those definitions should be understood to apply to the incorporated patent, application or publication in which they are found and not to the present application unless otherwise indicated.

Example 1

Manufacture of Transdermal Delivery System with Composite Backing

A thin layer of a stretchable or flexible polymer (1-40 mil) is laminated onto an occlusive backing (e.g. Scotchpak® 1012, polyester film laminate) with an adhesive such as polyisobutylene (PIB), acrylate, a silicone adhesive or other binding agent to form a laminate consisting of occlusive backing/adhesive/stretchable or flexible polymer.

An adhesive drug formulation is blended, coated on a release liner, and dried. The adhesive drug formulation is laminated on the stretchable or flexible polymer side of the backing laminate.

Example 2

Manufacture of Backing Laminate

A thin polyurethane film (0.5 to 1.0 mil) with a paper carrier (e.g. 3M COTran™ 9701 Backing, 2 mil polyurethane film) is used as the top layer. An occlusive backing, (e.g. Scotchpak® 1012, polyester film laminate) is laminated on the polyurethane film with an adhesive such as polyisobutylene (PIB), acrylate, a silicone adhesive or other binding agent to make a quad laminate consisting of a paper carrier/polyurethane/adhesive/occlusive backing.

The occlusive backing layer is kiss-cut to divide it into multiple, discrete pieces as attached on the flexible elastic layer such as a polyurethane film.

The size of each discrete occlusive backing piece ranges from about 10 cm2 to about 40 cm2 depending on requirements. Each of the discrete backing pieces are adhered or stuck together on the polyurethane film by the adhesive. The laminate may be rolled in further converting process.

Example 3

Manufacture of Transdermal Delivery System

An adhesive drug formulation is blended, coated on a release liner, and dried. The adhesive drug formulation is laminated on a discretely, kiss-cut occlusive film side of the backing laminate as prepared in Example 2. The paper carrier is removed from the polyurethane side to leave the final formulation laminate. It is die-cut into a required size which is a large patch containing multiple discrete pieces of occlusive film but all other layers are continuous. An exemplary patch is shown in FIG. 4B.

Example 4

In Vivo Adhesion Study of Transdermal Delivery System Comprising Segmented Intermediate Layer An in vivo adhesion study was performed to investigate the effect on patch adhesion by including a segmented patch layer as well as different patch configurations and formulations.

A control patch was formed comprising a flexible, occlusive backing comprised of a laminate of polyester and ethylene vinyl acetate copolymers (Scotchpak® 1012 available from 3M), an adhesive layer, and a release liner. The adhesive formulation consisted of 8.03 wt % fumed silica (Aerosil® 200P), 11.69 wt % propylene glycol, and 80.28 wt % Duro-Tak® 387-2287 adhesive. The adhesive was coated on a release liner and dried. A nonwoven PET fabric tie layer (Remay 2250) was imbedded between two adhesive layers. One of the release liners was replaced with the backing layer for form the final control laminate. The control patch was formed by cutting the final laminate to a suitable size rectangular patch.

A first segmented test patch was formed comprising flexible, occlusive backing comprised of a polyurethane film (3M 9832 Polyurethane film, 0.8 mil), an interfacing adhesive layer (polyisobutylene), a segmented intermediate layer, and a release liner. The occlusive backing layer was laminated to the interfacing adhesive layer. The intermediate layer was formed using the adhesive formulation as described above and cut into twelve separate pieces. The separated adhesive layer was laminated with the laminated backing/interfacing layer and a release liner. The laminate was cut to a suitable size rectangular patch.

A second segmented test patch was formed comprising a flexible, occlusive backing comprised of a woven polyethylene terephthalate (PET) KOB fabric (15 mil), a first interfacial adhesive layer (Duro-Tak® 387-2516 adhesive with a coat weight, 3 mg/cm$^2$), a second interfacial adhesive layer (a mixture of PIB adhesive with a coat weight of 5 mg/cm$^2$), a segmented intermediate layer, and a release liner.

The occlusive backing layer was laminated to the first and second interfacing adhesive layers. The intermediate layer was formed using the adhesive formulation as described above and cut into twelve separate pieces. The separated adhesive layer was laminated to the laminated backing/interfacing layers. The laminate was cut to a suitable size rectangular patch. FIG. 3 illustrates a patch according to the second segmented test patch.

In Vivo Adhesion Study

A control patch and a first or second segmented test patch was applied to intact, healthy skin on the back of each of 18 volunteers. Nine volunteers wore the patches with woven PET fabric/PIB layer and the other nine volunteers wore the patches with polyurethane/Duro-Tak® 387-2516/PIB layer.

Each patch was scored for the degree of adhesion to the skin every day for 7 days according to the following scale:

Score 0=≥90% (essentially no lift off the skin)
Score 1=≥75% to <90% (some edges only lifting off the skin)
Score 2=≥50% to <75% (less than half of the patch lifting off the skin)
Score 3=≥0% to <50% (more than half of the patch lifting off the skin)
Score 4=0 adhered—patch detached completely.

Each score was weighted by multiplying score by number of subjects having the score. All of the scores were added and averaged by dividing the total score by the total number of test subjects in order to calculate the daily average adhesion score over 7 days. The daily individual scores across the 7 days were averaged again to determine the 7 day mean adhesion score.

The 7 day mean adhesion scores were 1.3 for the woven PET fabric from KOB, 1.8 for 0.8 mil polyurethane film, and 2.2 for the control, respectively.

These results show the breathable top layer improved the adhesion with the segmented patch design significantly. The woven PET fabric performed better than polyurethane film as the breathable top layer.

Example 5

In Vivo Adhesion Study of Transdermal Delivery System Comprising Segmented Intermediate Layer An in vivo adhesion study was performed to investigate the effect on patch adhesion by including an overlaid border of the backing layer over a segmented patch layer.

A placebo adhesive formulation comprised layer comprised 15% Eudragit® EPO, 10 wt % triethyl citrate, 5 wt % SPAN 20, 10 wt % glycerin, 13 wt % Kollidon® CL-M, and 47 wt % of Duro-Tak® 387-2287 acrylate adhesive. A placebo adhesive layer was formed by laminating an occlusive backing (Scotchpak® 1012) with a layer of the placebo adhesive formulation (coat weight of 10 mg/cm$^2$ (2 mil)), a rate-controlling tie layer (Celgard® 2400), and a contact adhesive layer (5 w t % SPAN 20 (sorbitan monolaurate), 10 wt % triethyl citrate, 20 wt % Kollidon® CL-M and 65 wt % of Duro-Tak® 387-2287 (coat weight of 5 mg/cm$^2$)) to form an adhesive laminate.

A test patch was formed by placing an occlusive backing (Scotchpak® 1012) on top of the adhesive formulation layer and placing a release liner (Loparex® 7300) on the bottom of the contact adhesive layer.

A breathable top layer consisting of a woven PET fabric (KOB 053 bi-elastic fabric) was laminated to first and second interfacial adhesive layers. The first interfacial adhesive was Duro-Tak® 387-2516 with a coat weight of 3 mg/cm$^2$. The second interfacial adhesive was a mixture of PIB adhesive (80 wt %) and Kollidon® CL-M (20 wt %) with a coat weight of 5 mg/cm$^2$.

The test patches were cut into 12 pieces, which were integrated by placing the breathable top layer laminate over the patch (over the occlusive backing layer).

A control patch was prepared by integrating the breathable PET fabric/interfacial adhesive laminate such that the edge of the breathable top layer was flush with the integrated patch edge without extended border of the breathable laminate.

A first overlaid patch was formed by integrating the breathable PET fabric/interfacial adhesive laminate such that the edge of the breathable top layer extended beyond the integrated patch edge by 0.5 cm.

A second overlaid patch was formed by PET fabric/interfacial adhesive laminate such that the edge of the breathable top layer extended beyond the integrated patch edge by 1.0 cm.

Each of the control, first overlaid patch and second overlaid patch were assembled to a rectangular patch.

In Vivo Adhesion Study

A control patch and a first or second overlaid test patch was applied to intact, healthy skin on the back of each of 14 volunteers. Seven volunteers wore a control and a first overlaid patch (0.5 cm) and the other seven volunteers wore a control patch and a second overlaid patch (1.0 cm) for seven days.

Each of control, first overlaid patch and second overlaid patch were evaluated for their adhesion for 7 days in comparison to the control without border. Each patch was scored for the degree of adhesion to the skin every day for 7 days according to the scale as in Example 4.

Each score was weighted by multiplying the score by number of subjects having the score, and all the scores were added up and averaged by dividing total score by total number of test subjects to calculate daily average adhesion score every day over 7 days. The daily Individual scores across 7 days were averaged again to determine the 7 day mean adhesion score.

The 7 day mean adhesion scores were 0.2 for the patch with a 1.0 cm border, 1.8 for the patch with the 0.5 cm border, and 1.9 for the patch with no border, respectively. The border improved the adhesion of the patches with the patches having the 1.0 cm border and the patches remain adhered for all seven subjects for 7 days.

Example 6

In Vivo Adhesion Study of Transdermal Delivery System Comprising Segmented Intermediate Layer An in vivo adhesion study was performed to investigate the effect of adhesive layer patch design on patch adhesion.

A breathable top layer was prepared by laminating a 15 mil thick bi-elastic woven PET fabric (KOB 053 available from Karl Otto Braun GmbH & Co. KG), a first interfacial adhesive layer (Duro-Tak® 387-2516 (10 wt %) mixed with Duro-Tak® 387-2287 (90 wt %) with a coat weight of 3 mg/cm$^2$) and a second interfacial adhesive layer (a mixture of PIB adhesive (80 wt %) and Kollidon® CL-M (20 wt %) with a coat weight of 5 mg/cm$^2$).

A drug-in-adhesive layer (test formulation) comprised 2.59 wt % sodium bicarbonate, 10 wt % triethyl citrate, 2 wt % SPAN 20, 3 wt % lauryl lactate, 10 wt % glycerin, 15 wt % Kollidon® CL-M, and 57.41 wt % of Duro-Tak® 387-2287 acrylate adhesive. The drug-in-adhesive layer (coat weight 10 mg/cm$^2$, 2 mil) was laminated with a rate controlling membrane (Celgard® 2400), and a contact adhesive layer (2 wt % SPAN 20 (sorbitan monolaurate), 3 wt % lauryl lactate, 10 wt % triethyl citrate, 20 wt % Kollidon® CL-M and 65 wt % of Duro-Tak® 387-2287; coat weight of the contact adhesive was 5 mg/cm$^2$) to form an adhesive laminate. An occlusive backing (Scotchpak® 1012), the adhesive laminate and a release liner (Loparex® 7300) were laminated to form an intermediate layer. The occlusive backing and adhesive laminate layer were segmented into 12 pieces, which were integrated by placing the breathable top layer laminate over the patch (on the occlusive backing layer) to form the test patch. Two patches were prepared using the intermediate layer. For the first, the breathable top layer was placed so that the edge of the top layer was flush with the edge of the intermediate layer. For the second, the breathable top layer was placed so that the edge of the top layer extended beyond the first intermediate layer by 0.5 cm.

The control and test patch were a rectangular patch.

In Vivo Adhesion Study

The two different rectangular segmented patches, 0 and 0.5 cm borders, were evaluated for their adhesion for 7 days. A 0 and 0.5 cm overlaid patches were applied to intact, healthy skin on the back of each of 9 volunteers. Each volunteer had two patches with the same formulation, but different border/overlay applied. Each volunteer wore a patch having no overlay border (0 cm) and a second patch having an overhanging overlay border (0.5 cm). The patches were each worn for seven days.

Patches were tested for 9 volunteers in the same way as Example 4. Each volunteer wore two patches, one without a border and the other with a border, 0.5 cm. Each patch was scored for the degree of adhesion to the skin every day for 7 days in the same way as Example 4.

Each score was weighted by multiplying score by number of subjects having the score and all the scores were added up and averaged by dividing the total score by the total number of test subjects to calculate daily adhesion score every day over the 7 days. The averaged daily scores across the 7 days were averaged to determine the mean adhesion score for the 7 days.

The 7 day mean adhesion score was 0.5 for the 0.5 cm border and 1.0 for the control without border.

Example 7

Manufacture of Transdermal Delivery System with Composite Backing

A thin layer of KOB 053 woven polyester fabric (Karl Otto GmbH & Co.) is laminated onto a Scotchpak™ 1012 (3M®) polyester film laminate with Duro-Tak 87-2052, an acrylate copolymer pressure sensitive adhesive (Henkel Corporation) to form a laminate consisting of woven fabric/adhesive/polymer film.

An adhesive drug formulation is blended, coated on a release liner, and dried. The adhesive drug formulation is laminated on the polymer film side of the backing laminate.

Embodiments

1. A transdermal patch, comprising:
   a first backing layer comprised of an elastic material;
   an interfacing adhesive layer;
   a second backing layer comprised of a plurality of segments that are at least partially separated;
   an adhesive active agent layer comprising at least one active agent; and
   a release liner.
2. The transdermal patch of embodiment 1, wherein the second backing layer and the adhesive active agent layer together comprise a composite layer where the composite layer is comprised of a plurality of segments that are at least partially separated.
3. The transdermal patch of embodiment 1, wherein the plurality of segments are at least partially connected.
4. The transdermal patch of embodiment 2, wherein the plurality of segments are at least partially connected.
5. The transdermal patch of the combined or separate embodiments 1-4, wherein the first backing layer is comprised of an elastic polymer film, a multi-directional elastic woven fabric, a multi-directional elastic nonwoven fabric, a stretchable polymer film, a stretchable woven fabric, or a stretchable nonwoven fabric.
6. The transdermal patch of the combined or separate embodiments 1-5, wherein the polymer fabric or polymer film is comprised of one or more polymers selected from polyesters, polyethylenes, polypropylenes, polyvinylchloride, polyethylene vinyl acetate or copolymers thereof, and polyurethanes.
7. The transdermal patch of the combined or separate embodiments 1-6, wherein the first backing layer has a thickness of about 0.2-50 mil.
8. The transdermal patch of the combined or separate embodiments 1-7, wherein the interfacing adhesive layer is comprised of one or more polymers selected from selected from acrylates, acrylate copolymers, polyisobutylene, silicone, polystyrene butyl rubber, polyethylene vinyl acetate and copolymers thereof, and plasticized polymers.
9. The transdermal patch of the combined or separate embodiments 1-8, wherein the second backing layer is comprised of a material selected from an occlusive material and a breathable material.
10. The transdermal patch of the combined or separate embodiments 1-9, wherein the second backing layer is comprised of one or more polymers selected from polyesters, polyethylenes, polypropylenes, polystyrenes, polyvinylchloride, and a polyethylene terephthalate/ethylene vinyl acetate laminate.
11. The transdermal patch of the combined or separate embodiments 2 and 3-10, wherein the composite layer further comprises a tie layer positioned distal to the adhesive active agent layer.
12. The transdermal patch of embodiment 9, wherein the tie layer is a rate-controlling membrane that controls the rate of active agent release.
13. The transdermal patch of the combined or separate embodiments 2 and 3-12, wherein the composite layer further comprises a contact adhesive layer positioned between the adhesive active agent layer and the release liner.
14. The transdermal patch of the combined or separate embodiments 2 and 3-13, where each segment of the composite layer has a size of about 2-40 cm$^2$.
15. The transdermal patch of the combined or separate embodiments 1-14, wherein the interfacing adhesive layer comprises a first adhesive layer adjacent the first backing layer and a second adhesive layer adjacent the second backing layer.
16. The transdermal patch of the combined or separate embodiments 2 and 3-15, wherein at least the first backing layer and the release liner are sized to extend about 0.5-1.0 cm beyond the perimeter of the composite adhesive layer.
17. The transdermal patch of the combined or separate embodiments 1-16, wherein the release liner is comprised of a material selected from a silicone coated material, a fluorocarbon coated material, and a fluorosilicone coated material.
18. The transdermal patch of the combined or separate embodiments 1-17, wherein at least the first backing layer and the interfacing adhesive layers are laminated.
19. The transdermal patch of the combined or separate embodiments 2 and 3-18, wherein the layers of the composite layer are laminated.

20. The transdermal patch of the combined or separate embodiments 1-19, wherein the adhesive active agent layer is comprised of an adhesive matrix.

21. A method of transdermally administering an active agent, comprising:
removing a release liner from the transdermal patch of the combined or separate embodiments 1-20; and
adhering the transdermal patch to the skin of a patient for a period up to about 10 days to deliver the active agent to said patient.

22. A transdermal patch, comprising:
a first backing layer comprised of a flexible and breathable material;
an interfacing adhesive layer;
a second backing layer comprised of a plurality of segments that are at least partially separated;
an adhesive active agent layer comprising at least one active agent; and
a release liner.

23. The transdermal patch of embodiment 22, wherein the second backing layer and the adhesive active agent layer together comprise a composite layer where the composite layer is comprised of a plurality of segments that are at least partially separated.

24. The transdermal patch of the combined or separate embodiments 22-23, wherein the first backing layer is comprised of an elastic polymer film, a multi-directional elastic woven fabric, a multi-directional elastic nonwoven fabric, a stretchable polymer film, a stretchable woven fabric, or a stretchable nonwoven fabric.

25. The transdermal patch of the combined or separate embodiments 22-24, wherein the polymer fabric or polymer film is comprised of one or more polymers selected from polyesters, polyethylenes, polyurethanes, and nylon.

26. The transdermal patch of the combined or separate embodiments 22-25, wherein the polyester is selected from a polyester elastomer and polyester terephthalate.

27. The transdermal patch of the combined or separate embodiments 22-26, wherein the polyethylene is a polyethylene vinyl acetate copolymer.

28. The transdermal patch of the combined or separate embodiments 22-27, wherein the nonwoven or woven fabric is formed of one or more polymer fibers.

29. The transdermal patch of the combined or separate embodiments 22-28, wherein the one or more polymer fibers are formed of a polymer fiber selected from a polyester, cotton, silk, polypropylene, nylon, polystyrene, polyvinylchloride, and polyurethanes.

30. The transdermal patch of the combined or separate embodiments 22-29, wherein the first backing layer has a thickness of about 0.2-50 mil.

31. The transdermal patch of the combined or separate embodiments 22-30, wherein the second backing layer is comprised of an occlusive material.

32. The transdermal patch of the combined or separate embodiments 22-31, wherein the occlusive material is a polymer film or polymer laminate.

33. The transdermal patch of the combined or separate embodiments 22-32, wherein the polymer film or polymer laminate is comprised of polyesters, polyethylenes, polypropylenes, polystyrenes, polyvinylchloride, or nylon.

34. The transdermal patch of the combined or separate embodiments 22-33, wherein the polyethylene is a polyethylene vinyl acetate copolymer.

35. The transdermal patch of the combined or separate embodiments 22-34, wherein the second backing layer is comprised of a breathable material.

36. The transdermal patch of the combined or separate embodiments 22-35, wherein the composite layer further comprises a tie layer positioned distal to the adhesive active agent layer.

37. The transdermal patch of the combined or separate embodiments 22-36, wherein the composite layer further comprises a contact adhesive layer positioned between the adhesive active agent layer and the release liner.

38. The transdermal patch of the combined or separate embodiments 22-37, where each segment of the composite layer has a size of about 2-40 cm$^2$.

39. The transdermal patch of the combined or separate embodiments 22-38, wherein the interfacing adhesive layer is comprised of one or more adhesives selected from acrylates, polyisobutylene, silicone, polystyrene butyl rubber, polyethylene vinyl acetate and copolymers thereof, polyethylene terephthalate, and plasticized polymers.

40. The transdermal patch of the combined or separate embodiments 22-39, wherein the interfacing adhesive layer comprises a first adhesive layer adjacent the first backing layer and a second adhesive layer adjacent the second backing layer.

41. The transdermal patch of claim the combined or separate embodiments 22-40, wherein the first backing layer and/or the interfacing adhesive layer, and the release liner are sized to extend beyond a perimeter of the composite adhesive layer.

42. The transdermal patch of the combined or separate embodiments 22-40, wherein at least one of the first backing layer and the interfacing adhesive layer extends about 0.5-1.0 cm beyond the perimeter of the composite adhesive layer.

43. The transdermal patch of the combined or separate embodiments 22-41, wherein the release liner is comprised of a material selected from a silicone coated material, a fluorocarbon coated material, and a fluorosilicone coated material.

44. The transdermal patch of the combined or separate embodiments 22-43, wherein the second backing layer is impermeable to the at least one active agent.

45. The transdermal patch of the combined or separate embodiments 22-44, wherein at least the first backing layer and interfacing adhesive layers are laminated.

46. The transdermal patch of the combined or separate embodiments 22-45, wherein the layers of the composite layer are laminated.

47. The transdermal patch of the combined or separate embodiments 22-46, wherein the adhesive active agent layer is comprised of an adhesive matrix.

48. The transdermal patch of the combined or separate embodiments 22-47, wherein the segments of the composite adhesive layer are at least partially square or rectangular.

49. A method of transdermally administering an active agent, comprising:
removing a release liner from the transdermal patch of the combined or separate embodiments 22-48; and
adhering the transdermal patch to the skin of a patient for a period up to about 10 days to deliver the active agent to said patient.

50. A composite backing layer for use in a transdermal patch, comprising:
a first layer comprised of a polymer fabric or a polymer film;
a second layer comprised of one or more polymers having at least one of (i) a tensile strength of less than about 10 MPa and (ii) an elongation of at least about 10-50%;

a third layer comprised of one or more stretchable polymers having a stretchability of at least about 10%;
wherein the first and second layers are in contact and the second and third layers are in contact.

51. The composite backing layer of embodiment 50, wherein the polymer fabric or polymer film is comprised of one or more polymers selected from polyesters, polyethylenes, polypropylenes, polyvinylchloride, polyethylene vinyl acetate or copolymers thereof, and polyurethanes.

52. The composite backing layer of the combined or separate embodiments 50-51, wherein the first layer is selected from a woven, a non-woven polymer fabric, an occlusive polymer film, a polymer laminate, and a polymer/metal laminate.

53. The composite backing layer of the combined or separate embodiments 50-52, wherein the first layer has a thickness of about 0.5-20 mil.

54. The composite backing layer of the combined or separate embodiments 50-53, wherein the second layer is an adhesive layer.

55. The composite backing layer of embodiment 54, wherein adhesive layer is an adhesive tie layer.

56. The composite backing layer of the combined or separate embodiments 50-55, wherein the one or more polymers of the second layer are selected from acrylates, polyisobutylene, silicone, polystyrene butyl rubber, polyethylene vinyl acetate and copolymers thereof, and plasticized polymers.

57. The composite backing of the combined or separate embodiments 50-56, wherein the one or more polymers of the second layer have a low shear strength.

58. The composite backing layer of the combined or separate embodiments 50-57, wherein the second layer has a thickness of about 0.5-30 mil.

59. The composite backing layer of the combined or separate embodiments 50-58, wherein the third layer is a non-woven or woven fabric formed of one or more polymer fibers.

60. The composite backing layer of embodiment 59, wherein the one or more polymer fibers are formed of a polymer fiber selected from polyester, cotton, silk, polypropylene, nylon, polystyrene, polyvinylchloride, and polyurethanes.

61. The composite backing layer of the combined or separate embodiments 50-60, wherein the stretchable polymers have a stretchability of at least about 10% in at least one direction.

62. The composite backing layer of the combined or separate embodiments 50-61, wherein the third layer has a thickness of about 0.5-5 mil.

63. The composite backing layer of the combined or separate embodiments 50-62, wherein the third layer is attached to an adhesive drug layer comprising one or more drugs.

64. The composite backing layer of embodiment 63, wherein the backing layer is impermeable to the one or more drugs.

65. The composite backing layer of the combined or separate embodiments 50-64, wherein the backing layer is occlusive.

66. The composite backing layer of the combined or separate embodiments 50-65, wherein the first layer, second layer, and third layer are laminated.

67. The composite backing layer of the combined or separate embodiments 50-66, wherein the backing has a surface area of at least about 5-250 cm².

68. A transdermal patch for delivery of an active agent, comprising:
(a) a composite backing layer comprising:
a first layer comprised of a polymer fabric or a polymer film;
a second layer comprised of one or more polymers having at least one of (i) a tensile strength of less than about 10 MPa and (ii) an elongation of at least about 50%;
a third layer comprised of a material selected from one or more stretchable polymers having a stretchability of at least about 10%, a woven fabric and a non-woven fabric;
wherein the first layer, second layer, and third layers are arranged in contact as a composite;
(b) an adhesive drug layer comprising the active agent; and
(c) a release liner.

69. The transdermal patch of embodiment 68, wherein the first layer polymer fabric or polymer film is comprised of one or more polymers selected from polyesters, polyethylenes, polypropylenes, polyvinylchloride, polyethylene vinyl acetate or copolymers thereof, and polyurethanes.

70. The transdermal patch of embodiment 68, wherein the first layer is selected from an occlusive polymer film, a polymer laminate, a polymer/metal laminate, a breathable polymer film, a woven polymer fabric and a non-woven polymer fabric.

71. The transdermal patch of the combined or separate embodiments 68-70, wherein the first layer has a thickness of about 0.5-200 mil.

72. The transdermal patch of the combined or separate embodiments 68-71, wherein the second layer is an adhesive layer.

73. The transdermal patch of embodiment 72, wherein the adhesive layer is an adhesive tie layer.

74. The transdermal patch of the combined or separate embodiments 68-73, wherein the one or more polymers of the second layer are selected from acrylates, polyisobutylene, silicone, polystyrene butyl rubber, polyethylene vinyl acetate and copolymers thereof, and plasticized polymers.

75. The transdermal patch of the combined or separate embodiments 68-74, wherein the one or more polymers of the second layer have a low shear strength.

76. The transdermal patch of the combined or separate embodiments 68-75, wherein the second layer has a thickness of about 0.5-30 mil.

77. The transdermal patch of the combined or separate embodiments 68-76, wherein the third layer is a non-woven or woven fabric formed of one or more polymer fibers.

78. The transdermal patch of embodiment 77, wherein the one or more polymer fibers are formed of a polymer fiber selected from polyester, cotton, silk, polypropylene, nylon, polystyrene, polyvinylchloride, and polyurethanes.

79. The transdermal patch of the combined or separate embodiments 68-78, wherein the stretchable polymers have a stretchability of at least about 10% in at least one direction.

80. The transdermal patch of the combined or separate embodiments 68-79, wherein the third layer has a thickness of about 1-40 mil.

81. The transdermal patch of the combined or separate embodiments 68-80, wherein the backing layer is occlusive.

82. The transdermal patch of the combined or separate embodiments 68-81, wherein the backing layer is impermeable to the active agent.

83. The transdermal patch of the combined or separate embodiments 68-82, wherein the adhesive drug layer is comprised of an adhesive matrix.

84. The transdermal patch of the combined or separate embodiments 68-83, wherein the release liner is a silicone coated material.

85. The transdermal patch of embodiment 84, wherein the release liner is a silicone coated PET, fluorocarbon, or fluorocarbon coated PET.

86. The transdermal patch of the combined or separate embodiments 68-85, wherein the patch has a surface area of at least about 5-200 cm$^2$.

87. A transdermal patch for delivery of an active agent, comprising:
(a) a backing layer;
(b) an adhesive drug layer comprising the active agent;
(c) a tie layer embedded within the adhesive drug layer; and
(d) a release liner.

88. The patch of embodiment 87, wherein the tie layer is comprised of at least one polymer, a woven polymer fiber fabric, and a non-woven polymer fiber fabric.

89. A composite backing layer for use in a transdermal patch, comprising:
a first elastic or flexible layer comprised of one or more polymers having at least one of (i) a tensile strength of less than about 10 MPa or (ii) an elongation of at least about 50%;
a second adhesive layer; and
a third layer comprised of a plurality of separated pieces of an occlusive or substantially occlusive material.

90. The composite backing of embodiment 89, wherein the first layer is formed of a woven or non-woven polymer fabric or an elastic polymer film.

91. The composite backing of the combined or separate embodiments 89-90, wherein the elastic polymer film is selected from a polyurethane film, a thermoplastic polyester elastomer film, and a polyethylene vinyl acetate film.

92. The composite backing of the combined or separate embodiments 89-91, wherein the first layer has a thickness of about 0.5-20 mil.

93. The composite backing of the combined or separate embodiments 89-92, wherein the second adhesive layer is comprised of one or more adhesives.

94. The composite backing of embodiment 93, wherein the adhesive is selected from an acrylic adhesive, a polyisobutylene adhesive, and a silicone adhesive.

95. The composite backing of the combined or separate embodiments 89-94, wherein the second adhesive layer has a thickness of about 0.5-5 mil.

96. The composite backing of the combined or separate embodiments 89-95, wherein the occlusive or substantially occlusive material is selected from polyesters, polyethylenes, a polyethylene vinylacetate, polypropylenes, polystyrenes, polyvinylchloride or copolymers thereof, and nylon.

97. The composite backing of embodiment 96, wherein the third layer is a laminate.

98. The composite backing of the combined or separate embodiments 89-97, wherein the separated pieces are square or rectangular.

99. The composite backing of the combined or separate embodiments 89-98, wherein the third layer has a thickness of about 1-5 mil.

100. A method of transdermally administering an active agent, comprising:
removing a release liner from the transdermal patch or a patch comprising a backing of the combined or separate embodiments 22-99; and
adhering the transdermal patch to the skin of a patient for a period up to about 10 days to deliver the active agent to said patient.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, patent publications, and other publications mentioned herein are hereby incorporated by reference in their entirety. Where a patent, application, or publication contains express definitions, those definitions should be understood to apply to the incorporated patent, application or publication in which they are found and not to the present application unless otherwise indicated.

It is claimed:

1. A transdermal patch, comprising:
(a) a first backing layer comprised of an elastic material;
(b) an interfacing adhesive layer;
(c) a composite layer comprising a plurality of segments that are at least partially separated, the composite layer comprised of:
(i) a second backing layer, and
(ii) an adhesive active agent layer;
(d) a contact adhesive layer; and
(e) a release liner, wherein the contact adhesive layer is positioned between the adhesive active agent layer of the composite layer and the release liner.

2. The transdermal patch of claim 1, wherein the composite layer further comprises a tie layer positioned distal to the adhesive active agent layer.

3. The transdermal patch of claim 2, wherein the tie layer is a rate-controlling membrane that controls the rate of active agent release.

4. The transdermal patch of claim 1, wherein the plurality of segments of the composite layer are at least partially connected.

5. The transdermal patch of claim 1, wherein the first backing layer is comprised of an elastic polymer film, a polymer fabric, a multi-directional elastic woven fabric, a multi-directional elastic nonwoven fabric, a stretchable polymer film, a stretchable woven fabric, or a stretchable nonwoven fabric.

6. The transdermal patch of claim 1, wherein the first backing layer is comprised of one or more polymers selected from polyesters, polyethylenes, polypropylenes, polyvinylchloride, polyethylene vinyl acetate or copolymers thereof, and polyurethanes.

7. The transdermal patch of claim 1, wherein the first backing layer has a thickness of about 0.2-50 mil.

8. The transdermal patch of claim 1, wherein the interfacing adhesive layer is comprised of one or more polymers selected from selected from acrylates, acrylate copolymers, polyisobutylene, silicone, polystyrene butyl rubber, polyethylene vinyl acetate and copolymers thereof, and plasticized polymers.

9. The transdermal patch of claim 1, wherein the second backing layer of the composite layer is comprised of a material selected from an occlusive material and a breathable material.

10. The transdermal patch of claim 1, wherein the second backing layer of the composite layer is comprised of one or more polymers selected from polyesters, polyethylenes, polypropylenes, polystyrenes, polyvinylchloride, and a polyethylene terephthalate/ethylene vinyl acetate laminate.

11. The transdermal patch of claim 1, where each segment of the composite layer has a size of about 2-40 cm$^2$.

12. The transdermal patch of claim 1, wherein the interfacing adhesive layer comprises a first adhesive layer adjacent the first backing layer and a second adhesive layer adjacent the second backing layer of the composite layer.

13. The transdermal patch of claim 1, wherein at least the first backing layer and the release liner are sized to extend about 0.5-1.0 cm beyond the perimeter of the composite layer.

14. The transdermal patch of claim 1, wherein the release liner is comprised of a material selected from a silicone coated material, a fluorocarbon coated material, and a fluorosilicone coated material.

15. The transdermal patch of claim 1, wherein at least the first backing layer and the interfacing adhesive layers are laminated.

16. The transdermal patch of claim 1, wherein the second backing layer and the adhesive active agent layer of the composite layer are laminated.

17. The transdermal patch of claim 1, wherein the adhesive active agent layer of the composite layer is comprised of an adhesive matrix.

18. A method for transdermally administering an active agent, comprising:
   (i) removing a release liner from the transdermal patch of claim 1; and
   (ii) adhering the transdermal patch to the skin of a patient for a period up to about 10 days to deliver the active agent to said patient.

* * * * *